US012023362B2

(12) United States Patent
Galili et al.

(10) Patent No.: US 12,023,362 B2
(45) Date of Patent: Jul. 2, 2024

(54) THERAPEUTIC COMPOSITIONS AND METHODS OF USE FOR TREATING CANCER

(71) Applicant: AGALIMMUNE LIMITED, London (GB)

(72) Inventors: Uri Galili, London (GB); Stephen Shaw, London (GB); Michael Westby, London (GB)

(73) Assignee: AGALIMMUNE LIMITED, London (GB)

( * ) Notice: Subject to any disclaimer, the term of this patent is extended or adjusted under 35 U.S.C. 154(b) by 729 days.

(21) Appl. No.: 16/698,682

(22) Filed: Nov. 27, 2019

(65) Prior Publication Data

US 2020/0155626 A1    May 21, 2020

Related U.S. Application Data

(62) Division of application No. 15/564,774, filed as application No. PCT/GB2016/050973 on Apr. 7, 2016, now abandoned.

(30) Foreign Application Priority Data

Apr. 7, 2015 (GB) .................................. 1505860

(51) Int. Cl.
*A61K 38/45* (2006.01)
*A61K 9/00* (2006.01)
*A61K 35/761* (2015.01)
*A61P 35/00* (2006.01)
*A61P 35/02* (2006.01)
*C12N 7/00* (2006.01)
*C12N 15/86* (2006.01)

(52) U.S. Cl.
CPC .......... *A61K 35/761* (2013.01); *A61K 9/0019* (2013.01); *A61K 9/0031* (2013.01); *A61K 9/0034* (2013.01); *A61K 9/0043* (2013.01); *A61K 9/0053* (2013.01); *A61K 38/45* (2013.01); *A61P 35/00* (2018.01); *A61P 35/02* (2018.01); *C12N 7/00* (2013.01); *C12Y 204/01087* (2013.01); *C12N 2710/10332* (2013.01); *C12N 2710/10343* (2013.01); *C12N 2710/10371* (2013.01); *C12N 2710/16632* (2013.01); *C12N 2710/16643* (2013.01); *C12N 2710/16671* (2013.01)

(58) Field of Classification Search
CPC ...... A61K 35/761; A61K 38/45; C12N 15/86; C12N 2710/10332; C12N 2710/10343; C12N 2710/16632; C12N 2710/16643; C07H 21/04
See application file for complete search history.

(56) References Cited

U.S. PATENT DOCUMENTS

| 2002/0128221 A1 | 9/2002 | Schiff |
| 2003/0099616 A1 | 5/2003 | Irving et al. |
| 2003/0186850 A1 | 10/2003 | Clausen et al. |
| 2005/0201993 A1 | 9/2005 | Link et al. |

FOREIGN PATENT DOCUMENTS

| RU | 2536931 C2 | 12/2014 |
| WO | WO 2006/091515 A2 * | 8/2006 |
| WO | 2014089558 A1 | 6/2014 |

OTHER PUBLICATIONS

Chernajovsky et al (BMJ, 332: 1-3, 2006) (Year: 2006).*
Kaufman (Ann Surg Oncol (2021) 28:2432-2433) (Year: 2021).*
Zheng et al, (Mol Ther Oncolytics, 15: 234-247, 2019 (Year: 2019).*
Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Bulcha et al., 2021, Signal Transduction and Targeted Therapy, 6:53, p. 1-24.*
Anniina Koski et al: "Treatment of Cancer Patients With a Serotype 5/3 Chimeric Oncolytic Adenovirus Expressing GMCSF", Molecular Therapy, vol. 18, No. 10, Oct. 1, 2010 (Oct. 1, 2010), pp. 1874-1884, XP055015338, ISSN: 1525-0016, DOI: 10.1038/mt.2010.161.
Fueyo J et al: "A mutant oncolytic adenovirus targeting the Rb pathway produces anti-glioma effect in vivo" Oncogene, Nature Publishing Group, GB, vol. 19, No. 1, Jan. 6, 2000 (Jan. 6, 2000), pp. 2-12, XP002680362, ISSN: 0950-9232.
Kanerva et al (Int J Cancer, 110: 475-480, 2004). (Year: 2004).
Lucy Deriy et al: "In vivo targeting of vaccinating tumor cells to antigen-presenting cells by a gene therapy method with adenovirus containing the [alpha]1,3galactosyltransferase gene", Cancer Gene Therapy, vol. 12, No. 6, Apr. 8, 2005 (Apr. 8, 2005), pp. 528-539, XP055279376, GB ISSN: 0929-1903, DOI: 10.1038/sj.cgt.7700812.
Maxine Bauzon et al: "Armed Therapeutic Viruses—A Disruptive Therapy on the Horizon of Cancer Immunotherapy", Frontiers in Immunology, vol. 5, Jan. 1, 2014 (Jan. 1, 2014), XP055214432, DOI: 10.3389/fimmu.2014.00074.

(Continued)

*Primary Examiner* — Shin Lin Chen
(74) *Attorney, Agent, or Firm* — Aura IP Law, PC

(57) ABSTRACT

The present invention relates to compositions and methods for treating cancer. More specifically, the present invention relates to compositions of engineered oncolytic viruses for administration to a subject with cancer that specifically lyse tumor cells and actively target tumor cells and cell debris to antigen presenting cells, in order to generate anti-tumor immunity.

12 Claims, 10 Drawing Sheets

Specification includes a Sequence Listing.

(56) References Cited

OTHER PUBLICATIONS

Simona Bramante et al: "Treatment of melanoma with a serotype 5/3 chimeric oncolytic adenovirus coding for GM-CSF: Results in vitro, in rodents and in humans", International Journal of Cancer, vol. 137, No. 7, Mar. 26, 2014 (Mar. 26, 2015), pp. 1775-1783, XP055280194, US ISSN: 0020-7136, DOI: 10.1002/ijc.29536.
Tuve et al, (Journal of Virology, 80(24): 12109-12120, 2006). (Year: 2006).
Uri Galili: "Anti-Gal: an abundant human natural antibody of multiple pathogeneses and clinical benefits", Immunology., vol. 140, No. 1, Aug. 12, 2013 (Aug. 12, 2013), pp. 1-11, XP055280049, GB ISSN: 00192805, DOI: 10.1111/imm.12110.

* cited by examiner

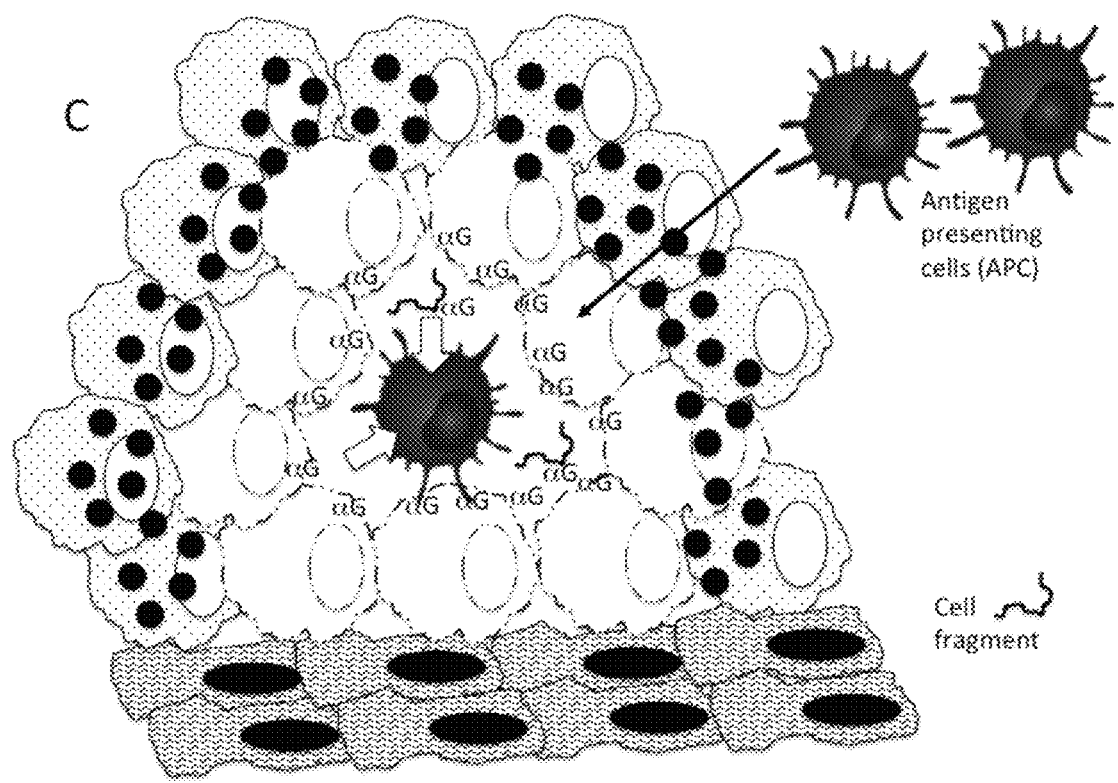
FIGURE 1 (ctd)

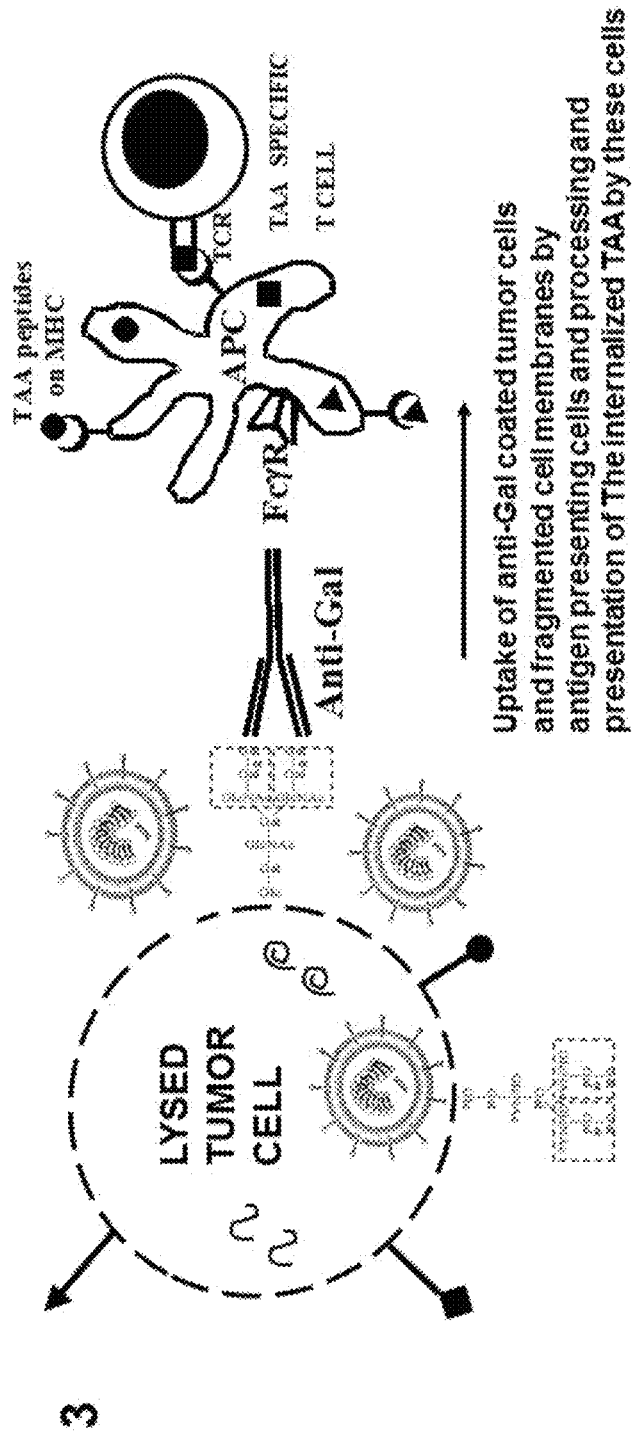
FIGURE 2 (ctd)

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer

<400> SEQUENCE: 1

```
atgaatgtca agggaaaag                                                 19

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
tcagacatta tttctaacca                                                20

<210> SEQ ID NO 3
<211> LENGTH: 8
<212> TYPE: PRT
<213> ORGANISM: Artificial Sequence
<220> FEATURE:
<223> OTHER INFORMATION: Murine

<400> SEQUENCE: 3

Leu Thr Cys His Glu Ala Gly Phe
1               5
```

THERAPEUTIC COMPOSITIONS AND METHODS OF USE FOR TREATING CANCER

CROSS-REFERENCE TO RELATED APPLICATIONS

This application claims priority as a divisional application under 35 U.S.C. § 121 to U.S. application Ser. No. 15/564,774, entitled "THERAPEUTIC COMPOSITIONS AND METHODS OF USE FOR TREATING CANCER," filed Oct. 6, 2017, which is as a U.S. National Stage entry under 35 U.S.C. § 371 of International Application No. PCT/GB2016/050973 filed on Apr. 7, 2016, designating the United States of America and published in English on Oct. 13, 2016, which in turn claims priority to Great Britain Patent Application 1505860.5 filed on Apr. 7, 2015, each of which is hereby incorporated by reference in its entirety.

FIELD OF THE INVENTION

The present invention relates to compositions and methods for treating cancer. More specifically, the present invention relates to compositions of engineered oncolytic viruses for administration to a subject with cancer that specifically lyse tumor cells and actively target tumor cells and cell debris to antigen presenting cells, in order to generate anti-tumor immunity.

REFERENCE TO A SEQUENCE LISTING SUBMITTED ON COMPUTER

The content of ASCII text file of the sequence listing named "2019-11-27-SequenceListing-SGTRS-011US0D1" which is 4 kb in size with a created date of Nov. 27, 2019 and electronically submitted via EFS-Web herewith the application, is incorporated herein by reference in its entirety.

BACKGROUND OF THE INVENTION

Tumors may develop in cancer patients because the immune system fails to detect tumor cells as cells that ought to be destroyed. Tumor cells express autologous tumor antigens in a large proportion of cancer patients. These autologous tumor antigens, also called "neoantigens", may elicit a protective anti-tumor immune response. Tumor cells, or tumor cell membranes, have to be internalized by antigen presenting cells in order to induce the development of an anti-tumor immune response. However, the immune system in many cancer patients displays an "ignorance" toward the tumor antigens that is associated with early development of the tumor in a "stealthy" way, so that the tumor is effectively "invisible" to antigen presenting cells (Pardoll, 2000; Clin Immunol. 95:844-49, and Dunn et al, 2002; Nat Immunol; 3: 991-8).

In addition, the tumor microenvironment and local cytokine milieu are often suppressive toward immune function and can actively induce immune cell anergy and death (Malmberg, Cancer Immunol Immunother., 53: 879-92; Lugade et a; J Immunol. 2005; 174: 7516-23 (2004); Schreiber et al., Science (New York, N.Y.), 331(6024), 1565-70 (2011)). Effective treatment of tumor lesions requires two components: 1. Destruction of the lesions that are large enough to be detected visually or by imaging technology, and 2. Induction of a protective, systemic anti-tumor immune response against tumor antigens. Such an immune response will destroy any untreated lesions (for example, those that cannot be accessed for treatment nor removed by surgery) and results in immune mediated detection, regression, and/or destruction of micrometastases which cannot be detected visually and are not detectable by imaging. Often, the size of a tumor impedes the efficacy of a circulating anti-tumor immune response in a timely manner.

Surgical resection or other means such as intratumoral injection of compositions are often necessary to reduce the size of a tumor in addition to harnessing an active anti-tumor immunity.

Recently, oncolytic viruses have been developed that are useful in selectively killing tumor cells by lytic replication and thereby reducing tumor size (Liu et al., World J Gastroenterol. 2013 Aug. 21; 19(31):5138-43). Useful viruses are disabled such that they are no longer pathogenic, i.e. do not replicate in and kill non-tumor cells, but such that they can still enter and kill tumor cells. One exemplary virus, herpes simplex virus (HSV), has been suggested to be of use for the oncolytic treatment of cancer. A number of mutations to HSV have been identified which still allow the virus to replicate in culture or in actively dividing cells in vivo (e.g. in tumors), but which prevent significant replication in normal tissue.

Promise has been shown for various additional viruses, in addition to HSV, for the oncolytic treatment of cancer. The combined use of an oncolytic HSV with the delivery of the gene encoding an immunomodulatory protein, granulocyte macrophage colony stimulating factor (GM-CSF), encoded in the disabled virus genome has been shown to have immune stimulating properties against the tumor to be treated, particularly after inactivation of viral functions which usually reduce immune responses to HSV. Thus in such use an oncolytic HSV mutant would be inoculated into a primary or secondary tumor where replication and oncolytic destruction of the tumor would occur. The problem with this approach is that GM-CSF is used to recruit antigen-presenting cells to the lesion site, but uptake of tumor material by these cells thereafter is random. Antigen-presenting cells are quite effective in taking up small particulate material and soluble antigens but are inefficient at internalizing cells or larger cell fragments.

Induction of a protective anti-tumor immune response requires uptake of the tumor cells and cell components by antigen-presenting cells, then processing of tumor antigens and their transportation by antigen presenting cells to the draining lymph nodes. In the lymph nodes, the immunogenic tumor antigen peptides are presented by antigen presenting cells in association with class I or class II MHC molecules for the activation of tumor specific $CD8^+$ and $CD4^+$ T cells, respectively. Only after these T cells are activated by the processed and presented tumor antigen peptides, these lymphocytes proliferate, leave the lymph nodes and circulate in the body to seek and destroy metastatic tumor cells expressing the relevant tumor antigens. Therefore, eliciting an effective anti-tumor immune response requires effective and active targeting of tumor cells to antigen presenting cells.

What is therefore needed is compositions and methods to non-surgically reduce tumor size through cell lysis and active targeting of tumor cells, cell debris and membrane fragments for antigen presenting cell recruitment and ensuing immune response. Also needed are ways to increase the efficiency of tumor cell and cell fragment internalization by antigen presenting cells within the tumor microenvironment.

SUMMARY OF THE INVENTION

According to a first aspect of the invention, there is provided an oncolytic virus comprising a nucleic acid encoding a hexosyl transferase enzyme.

According to a further aspect of the invention, there is provided a pharmaceutical composition comprising the oncolytic virus as defined herein in combination with a pharmaceutically acceptable carrier.

According to a further aspect of the invention, there is provided a method of treating an individual with a neoplasm which comprises the steps of:
 i) expressing an endogenous enzyme delivered by the oncolytic virus as defined herein in at least one cancer cell to modify cell membrane glycosylation; and
 ii) inducing lysis of the at least one cancer cell resulting from administration of the oncolytic virus.

According to a further aspect of the invention, there is provided a method of treating cancer comprising administering a therapeutically effective amount of the oncolytic virus as defined herein to a patient suffering from cancer or having a neoplasm or tumor in need of treatment.

DETAILED DESCRIPTION OF THE INVENTION

Figure 1:
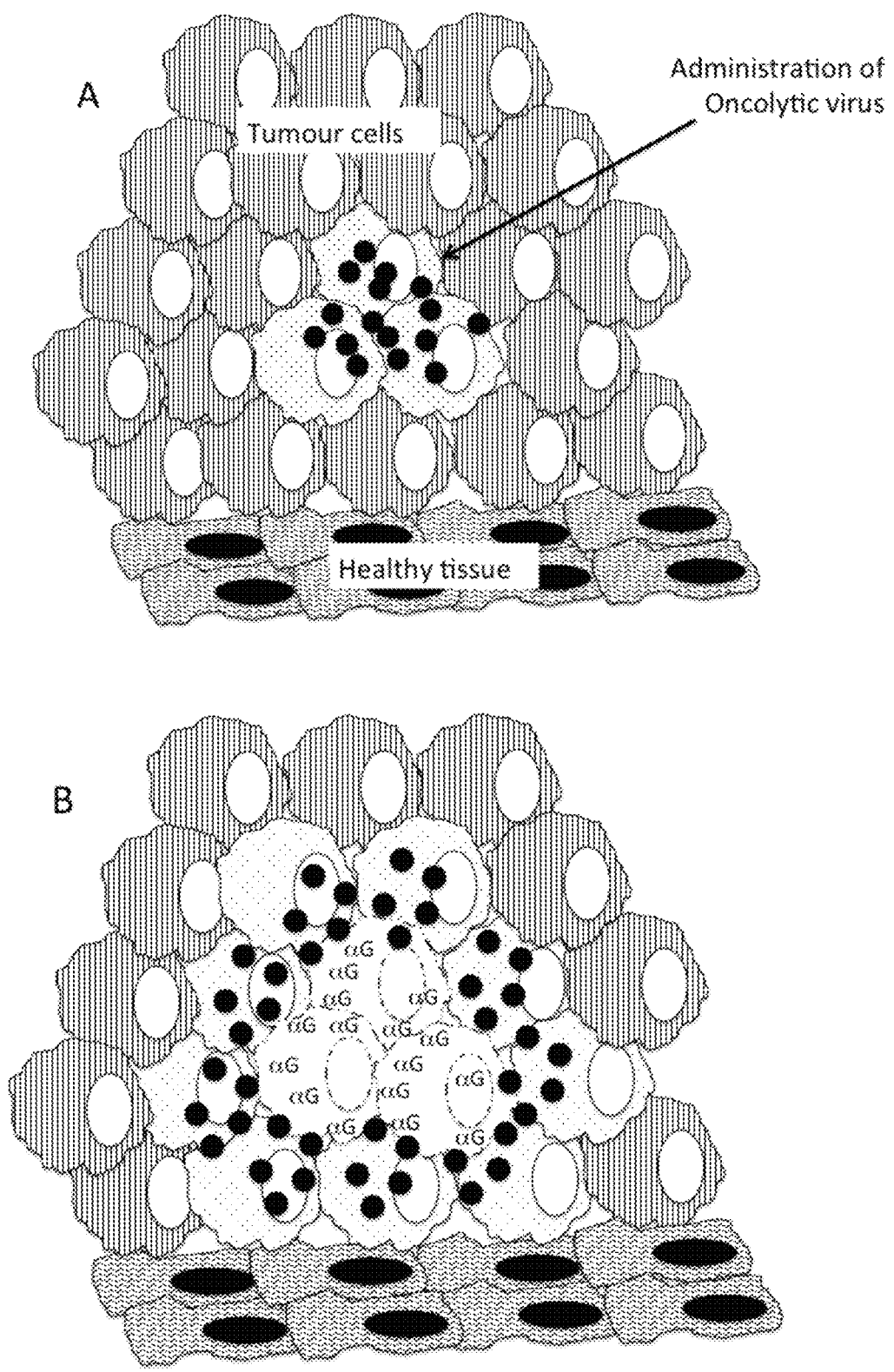
FIG. 1: Provides a schematic showing a series of cellular events relevant to the present methods. These events include A) administration of engineered viral compositions, B) infection, replication, expression of alpha 1,3-galactosyltransferase, and alpha-gal epitopes, and C) oncolysis and recruitment of antigen presenting cells at the tumor site.

According to a first aspect of the invention, there is provided an oncolytic virus comprising a nucleic acid encoding a hexosyl transferase enzyme.

The present invention relates to compositions and methods to combine oncolytic virus-induced lysis of tumor cells with active immune-mediated targeting and recruitment of antigen presenting cells (APCs) to a tumor site. Engineered oncolytic viruses that express a hexosyltransferase, such as alpha 1,3-galactosyltransferase, will modify the glycosylation of infected cells such that they express alpha-gal epitopes on cell membranes prior to virus-induced lysis. When the tumor cells are subsequently lysed by the virus, the cell membrane fragments will be opsonized by natural anti-Gal antibodies that bind the alpha-gal epitopes to form immune complexes. The anti-Gal antibodies will enhance the phagocytosis of the tumor cell fragments by APCs through the interaction between the Fc region of the anti-Gal antibodies and Fcγ receptors (FcγR) on the APCs. Similarly, intact tumor cells that express alpha-gal epitopes after virus infection will also be opsonized by anti-Gal and taken up by APCs via FcγRs. Uptake of antigen via FcγRs results in activation and maturation of APCs, which process the tumor antigens for presentation on MHC molecules and migrate to the draining lymph nodes, where they present the tumor antigens to T cells. By this process a protective immune response is generated against the patient's own tumor antigens.

In addition to the above, expression of alpha-gal epitopes on the cell surface, and their subsequent complexation with anti-Gal antibodies, will lead to activation of complement. Activation of complement results in: release of chemotactic peptides that recruit APCs to the tumor; opsonization of intact tumor cells and tumor cell membrane fragments with complement C3b molecules; complement-mediated lysis of intact tumor cells. Intact tumor cells and tumor cell fragments opsonized with complement C3b molecules are bound and internalized by APCs via the interaction between C3b and complement receptors on the APC.

Therefore, in addition to oncolytic virus-induced lysis of infected tumor cells, the opsonization of tumor cells and cell fragments with anti-Gal antibodies and the subsequent activation of complement and formation of immune complexes, which are phagocytosed by APCs, results in a protective anti-tumor immune response. Therefore, disrupting a tumor mass by the combination of virus-induced oncolysis and immune-activation is improved over separate administration of either a non-replicative alpha 1,3-galactosyltransferase-expressing virus, or a replication-competent non-alpha 1,3-galactosyltransferase-expressing oncolytic virus alone.

The present invention thus provides an improved treatment of various types of cancer, and even the treatment of such types that have as of yet been thought to be not curable is possible.

The present invention is directed to compositions and methods of using oncolytic viruses that have been modified to deliver a heterologous nucleic acid sequence encoding a glycosyl transferase gene, such as alpha 1,3-galactosyltransferase. The premise being that the virus specifically infects tumor cells, which then produce and express the functional alpha 1,3-galactosyltransferase enzyme. The alpha 1,3-galactosyltransferase enzyme subsequently produces and integrates alpha-gal epitopes on the surface of the tumor cells. The integration of alpha-gal epitopes on the tumor cell membrane occurs prior to cell lysis induced by the oncolytic virus, such that the subsequent cellular membrane debris is labeled with alpha-gal epitopes. Without wanting to be bound by any specific mechanism, it is believed that binding of alpha-gal labeled tumor cell fragments by the natural anti-Gal antibody activates the complement system (as do most antigen/antibody interactions) and generates complement cleavage chemotactic factors that recruit APCs to the treated tumor. The tumor cells and tumor cell membrane fragments that express alpha-gal epitopes are opsonized by anti-Gal and actively targeted for phagocytosis by the APCs recruited to the tumor. It is believed that the approach described herein is mechanistically different from previous oncolytic virus approaches that express GM-CSF, where the APCs randomly internalize soluble molecules that are in their vicinity by pinocytosis with minimal phagocytosis of particulate material. In the present approach, tumor cell membranes are more efficiently phagocytosed by APCs because the tumor cell fragments or intact tumor cells express alpha-gal epitopes, which subsequently bind anti-Gal antibodies. The interaction between the Fc portion of the anti-Gal antibodies coating the tumor cell fragments/intact tumor cells and the FcγRs on APCs stimulate the APCs to internalize, process and present the antigens to T cells. Additionally, the activation of complement and the subsequent opsonization of the tumor cell fragments and intact tumor cells with complement protein C3b enables APCs bearing complement receptors to effectively internalize, process and present tumor antigens to T cells.

The present methods are counter intuitive because one would not presumably seek to modify tumor cell surface glycosylation with a replication competent oncolytic virus to target the cell membrane fragments and intact cells for uptake by APCs.

Figure 2:
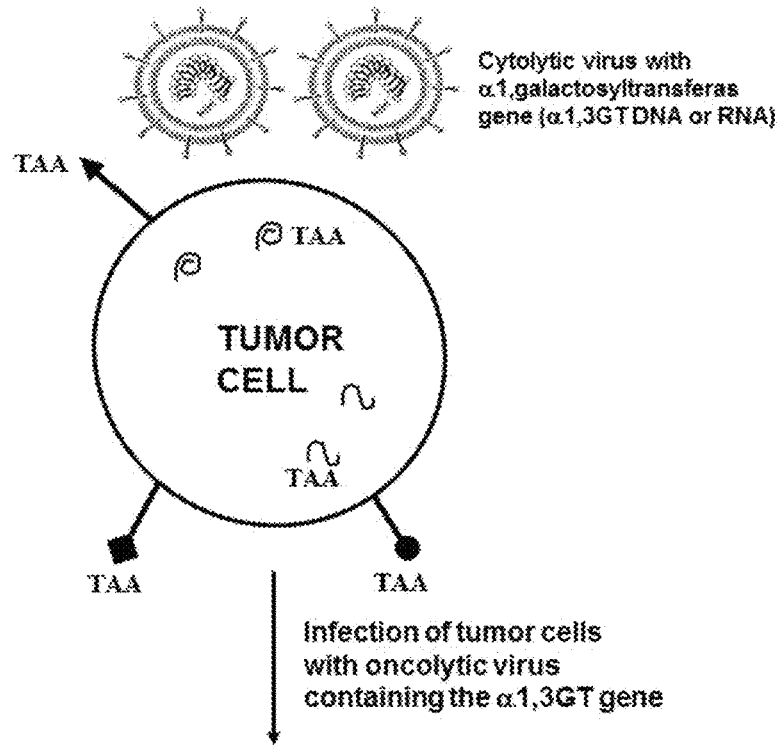
FIG. 2: Provides a schematic showing a tumor cell infected with oncolytic virus containing alpha 1,3-galactosyl transferase and expressing alpha-gal epitopes on its cell surface prior to lysis. Alpha-gal-labelled membrane fragments are internalized by antigen-presenting cells. (1) Tumor cells contain tumor associated antigens (TAA) in the cytoplasm and on the cell membrane, which are unique to the tumor and to each individual patient. These TAA are presented on the cell membrane as (●, ▲, ■) and as protein molecules inside the cell (spirals and wavy lines). The oncolytic virus (filled circles with 11 external spokes) introduced into the tumor lesion contains the alpha 1,3-galactosyltransferase gene inserted into its genome. (2) The oncolytic virus infecting the tumor cells introduces the alpha 1,3-galactosyltransferase gene into the tumor cells. This gene is transcribed and translated within the infected cell resulting in the production of the alpha 1,3-galactosyltransferase ($\alpha$1,3GT) enzyme. This enzyme synthesizes alpha-gal epitopes on cell surface glycoproteins, glycolipids and proteoglycans. Binding of the natural anti-Gal antibody to these alpha-gal epitopes activates the complement system and thus generates chemotactic factors in the form of complement cleavage peptides that recruit antigen presenting cells into the treated tumor lesion. (3) The tumor cells are lysed by the oncolytic virus and by anti-Gal binding to the alpha-gal epitopes on the cell membranes by complement-dependent cytotoxicity and by antibody-dependent cellular cytotoxicity (ADCC). The dead cells and fragmented cell membranes coated with the anti-Gal antibody (that is bound to the alpha-gal epitopes), are internalized by antigen presenting cells (APC) via interaction between the Fc portion of the anti-Gal antibody coating the cells, or cell membranes, and Fc$\gamma$ receptors on the APC. TAAs internalized as a result of this uptake are processed by the APC, and the TAA peptides are then presented on the APC cell membrane in association with MHC molecules. The APCs migrate to the draining lymph nodes where the presented TAA peptides bind to the T cell receptors of tumor specific T cells. These T cells are activated as a result of this interaction. The activated tumor specific T cells proliferate and leave the lymph nodes in order to circulate, detect and destroy metastatic tumor cells.
Figure 2:
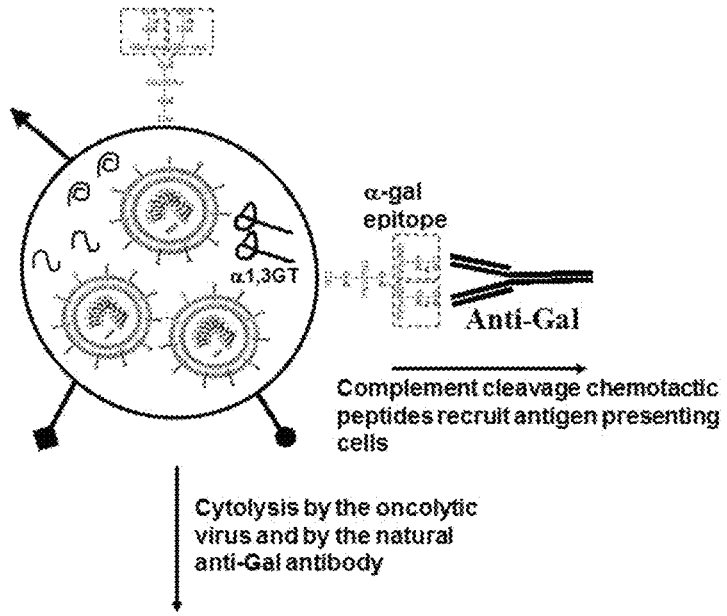

The expression and cell membrane integration of alpha-gal epitopes prior to virus-induced cell lysis provides a method to label tumor cell membrane fragments for APC recruitment and active uptake by APCs, inducing a protective anti-tumor immune response as compared to the less efficient methods previous described. While not to be limited by any specific mechanism, schematics are provided in FIGS. 1 and 2 which show one possible mechanism by which it is believed that the claimed compositions and methods have therapeutic action.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

In one embodiment, the enzyme is a galactosyl transferase enzyme. In a further embodiment, the enzyme is an alpha 1,3-galactosyltransferase enzyme.

I. Compositions

The compositions useful herein comprise an oncolytic virus and a nucleic acid sequence encoding a galactosyl transferase and optionally a pharmaceutically acceptable carrier useful for administration. Thus, according to a further aspect of the invention, there is provided a pharmaceutical composition comprising the oncolytic virus as defined herein in combination with a pharmaceutically acceptable carrier.

A. Viruses

In one embodiment, the virus is engineered to be oncolytic. In an alternative embodiment, the virus is naturally oncolytic.

In one embodiment, the oncolytic virus comprises a recombinant binding domain specific for a tumor stem cell marker.

In one embodiment, the virus is replication restricted and only lyses cancer cells leaving non-cancer cells.

Replication-restrictive oncolytic viruses are particularly useful for the compositions and methods described herein. Such viruses only replicate in and kill cancer cells. They may additionally encode a heterologous gene (or genes) that encodes for a protein, which has additional anti-tumor properties. The term oncolytic virus is meant to comprise any virus that infects/enters and lyses cancer cells. The ideal oncolytic virus efficiently kills a clinically relevant fraction of the patient's cancer cells by direct cytolysis with a minimal destruction of non-neoplastic tissue.

Oncolytic viruses are preferred (from a safety perspective) if they naturally are not pathogenic (e.g. naturally do not infect humans) or only cause mild disease in humans (e.g. adenoviruses cause flu-like symptoms). Viruses that have been used successfully in approved vaccines and have been administered to thousands or millions of people (e.g. small pox vaccine) are also preferred for this reason. If a virus is pathogenic in humans and is linked to significant disease (e.g. neurotoxicity associated with some herpes virus strains) then it is preferred to make multiple deletions or mutations in the viral genome to render them specific for cancer cells and reduce the risk that a single genetic recombination event with an endogenous virus leads to a fully pathogenic strain.

Targeted tumor cell entry and specificity of replication are desirable. Furthermore, the virus should be safe and apathogenic when applied in patients. Oncolytic viruses derived from many different types of viruses have been described by Liu et al. (Liu et al., Nature Clinical Practice Oncology 4: (2) 101-117, 2007). Among these enveloped viruses such as, but not limited to herpes simplex virus (HSV), vaccinia virus (VV) and paramyxoviruses such as measles virus (MeV), Newcastle disease virus (NDV) or rhabdoviruses like vesicular stomatitis virus (VSV), are most prominent. Besides applying unmodified wildtype virus, genetic engineering can further improve safety and efficacy of oncolytic viruses.

A key feature of replication restrictive oncolytic virus vectors that encode a heterologous gene is that the initial dose of heterologous gene can be amplified in vivo many fold by replication in, and release from, cancer cells within the injected lesion(s). This is taught, for example, by Liu et al (Liu at al., 2003), who describes the features of a mutant herpes simplex virus-1 (HSV-1) vector that encodes granulocyte macrophage-colony stimulating factor (GM-CSF). Collectively, these cancer therapies have been termed "armed therapeutic vaccines" (Bauzon & Hermiston, 2014). Engineering the envelope proteins can restrict virus infection to tumor cells and insertion of suicide genes can enhance therapeutic effects (Nakamura et al., Expert Opin. Bio. Ther. 4: (10): 1685-1692, 2004); Liu et al., Nature Clinical Practice Oncology 4: (2) 101-117, 2007; Liu et al., Gene Therapy, 10(4), 292-303, 2003).

Viruses may be derived from well-characterized lab-adapted strains that have been maintained by multiple serial passages through immortalized cell lines in tissue culture. However, human tumors in patients grow more slowly than do immortalized cell lines in optimized culture conditions, and may have other environmental and development factors that limit the rate of metabolism and cell division (such as the hypoxic environment that can exist at the center of a large tumor mass, a result of an insufficient nutrient supply). Therefore, it is preferable to select a virus for optimal growth in vivo (in situ) rather than based on its growth characteristics in tissue culture. For example, an HSV-1 strain derived from clinical isolate JS1 (obtained from a patient and having only undergone a short time of propagation in tissue culture) has been used to generate oncolytic viruses for treatment of cancer patients (Liu, 2003). An important consideration in selecting a clinical isolate is that optimal conditions can be identified such that it can be propagated in vitro, which is necessary for scale up and manufacture of the clinical material. Mutations to the genome are envisaged that improve the replication of virus in tissue culture without impairing its growth in tumors in vivo.

In addition to selecting a virus vector based on its ability to replicate in and lyse tumor tissue in patients, additional mutations to the genome are envisaged that further improve its ability to replicate in vivo. For example, two genes are deleted from clinical HSV-1 strain, JS1 (Liu, 2003). The first deletion, ICP34.5, restricts virus replication to cancer cells; the second, ICP47, results in the early expression of US11, which encodes a viral protein that blocks phosphorylation of host protein, PKR. PKR is a key component of the innate immune response to viral infection—upon phosphorylation it shuts down protein translation in infected cells and limits viral replication. Therefore, the in vivo replication of the mutant JS1 ICP34.5-/ICP47-strain is enhanced relative to the wild type (non-mutated) strain.

In various embodiments, the oncolytic virus is an oncolytic replication competent adenovirus, vaccinia virus, herpes virus, reovirus, measles virus or Newcastle disease virus.

In another embodiment, the virus is an RNA or DNA based virus of human or non-human origin, such as adenovirus, herpesvirus, vaccinia virus, measles virus, Newcastle Disease Virus, autonomous parvoviruses, vesicular stomatitis virus (VSV) or reovirus.

Exemplary oncolytic viruses shown in Table 1 are currently in clinical trials and may be modified as described herein for use in the therapeutic methods provided. In different embodiments the oncolytic virus is an enveloped virus derived from the virus families herpesviridae, poxviridae, rhabdoviridae, or paramyxoviridae, preferably from the Paramyxoviridae family, genus Morbillivirus.

TABLE 1

Clinically Evaluated Oncolytic Viruses

| VIRUS | NAME | CANCER TYPE |
|---|---|---|
| Adenovirus | ONYX-015 H101 | SCCHN |
| | | Glioma |
| | | Ovarian |
| | CGTG-102 | Solid Tumors |
| | CG0070 | Bladder |
| | ICOVIR-5 | Solid Tumors |
| | ColoAd1 | Colorectal |
| Vaccinia Virus | GLONC1 | Solid Tumors |
| | JX-594 | Liver Tumors |
| | | Solid Tumors IV |

TABLE 1-continued

Clinically Evaluated Oncolytic Viruses

| VIRUS | NAME | CANCER TYPE |
| --- | --- | --- |
| Herpesvirus | G207 | Glioma |
| | NV1020 | Liver Tumors IA |
| | TVec | Breast |
| | | SCCHN |
| | | Melanoma IT |
| | | Liver Tumors |
| Reovirus | Reolysin | SCCHN IT |
| | | Solid Tumors IV |
| Measles Virus | MV-CEA | Ovarian IP |
| | MV-NIS | Ovarian IP |
| | | Glioma IT |
| | | Myeloma IV |
| | | Mesothelioma |
| NDV | PV701 | Solid Tumors |

From Bauzon & Hermiston, 2014

Some oncolytic viruses are genetically modified to confer tumor-specific replication (adenovirus, herpesvirus, vaccinia virus) while others are naturally tumor-specific viruses (reovirus, Newcastle disease virus, autonomous parvovirus, certain measles strains, and vesicular stomatitis virus (VSV)).

i) Adenovirus

In one embodiment, the oncolytic virus is an adenovirus. Data is presented herein in Examples 1-3 and 8 and FIGS. 4-9 which demonstrates positive results achieved using alpha 1,3-galactosyltransferase containing adenoviruses. Human adenoviruses are non-enveloped, double-stranded DNA viruses of about 30-38 kB. A key feature of adenoviruses is that they encode a number of viral proteins that inhibit critical host regulatory proteins. Some of these host regulatory proteins (such as p53) are defective in many cancers. Therefore, deletion of the viral gene renders the mutant viruses selective for replication in cancers with the defective regulatory host protein.

Thus, mutation of the adenovirus E1B-55kD gene, a p53-inhibitory protein, (for example in the virus dl1520), is selective for tumors that have limited or no p53 function. p53 function is lost in most human cancers through various mechanisms including gene mutation, overexpression of p53-binding inhibitors (e.g. mdm2, human papillomavirus E6), and loss of the p53-inhibitory pathway modulated by p14$^{ARF}$.

Similarly, deletions in the E1a conserved region 2 have defective retinoblastoma (RB) protein binding, and these mutants are being evaluated for use against tumors with RB pathway abnormalities (for example in the virus d/922/947).

Another approach to obtain cancer-cell selective replication of adenoviruses is to control expression of the viral E1a gene product using a promoter that is specific for the tissue or cancer of interest. For example, this has been applied to oncolytic adenoviruses targeting prostate cancer (by genetic modification of the genome to introduce the prostate specific antigen (PSA) promoter/enhancer upstream of the E1a gene.

In one embodiment, the virus is a conditionally replicating adenovirus (CRAd), in which replication is restricted to tumor cells. CRAds have been demonstrated to selectively replicate in cancer cells, causing their lysis and death (Fueyo et al., 2000; Kanno et al., 2012; Bramante et al., 2015). CRAds have been generated using adenovirus 5 (Ad5) that has been genetically modified to express the fiber knob of adenovirus 3 (Ad3), to create an Ad5/3 chimeric virus (Kanerva et al., 2003; Kim et al., 2013).

Thus, in one embodiment, the CRAd is an Ad5/3 chimeric virus. The chimeric Ad5/3 virus is able to bind to cells and gain entry using CD46, the Ad3 receptor, rather than the coxsackie-adenovirus receptor (CAR), which bound by Ad5. This is advantageous as many tumors have variable expression of CAR, whereas all nucleated cells express CD46 (Ulasov et al., 2006). The virus is rendered conditionally replicative by introducing a 24-base pair deletion (Δ24) in constant region 2 (CR2) of the viral immediately early (E1a) gene (Kanerva et al., 2003). Thus, in one embodiment, the Ad5/3 chimeric virus additionally comprises a 24-base pair deletion (Δ24) in constant region 2 (CR2) of the viral immediately early (E1a) gene, herein known as the Ad5/3-Δ24 CRAd. This mutation results in a viral E1a protein that is unable to bind retinoblastoma (Rb) protein for induction of S phase within the cell (Fueyo et al., 2000). Therefore, the virus is unable to replicate in non-dividing normal cells, but efficiently replicates in cells that have an inactive Rb/p16 pathway, a phenotype indicated to be shared by all cancers (Sherr, 1996). Chimeric, conditionally replicating Ad5/3-Δ24 CRAd can be further modified by the substitution of the adenovirus early region (E3) gene with a transgene, which results in an Ad5/3-Δ24 CRAd that specifically produces the transgene during replication (Koski et al., 2010; Kanerva et al., 2013; Bramante et al., 2015). The chimeric, conditionally replicating Ad5/3-Δ24 CRAd has been further modified by the substitution of the adenovirus early region (E3) gene with an alpha 1,3-galactosyltransferase transgene, which results in an Ad5/3-Δ24 CRAd that specifically produces alpha 1,3-galactosyltransferase during replication. Thus, in one embodiment, the Ad5/3-Δ24 CRAd additionally comprises an alpha 1,3-galactosyltransferase transgene, herein known as CRAd-αGT. Data is presented herein in Example 8 and FIGS. 6-9 which demonstrates that human lung carcinoma and melanoma cells infected with CRAd-αGT express alpha-gal epitopes on the cell surface and are bound by anti-Gal antibodies prior to virus-induced lysis.

ii) Herpes Virus

In one embodiment, the oncolytic virus is a herpes virus. Methodology is presented herein in Examples 4-7 which demonstrates how positive results may be achieved using alpha-1,3 galactosyltransferase containing herpes virus. Herpes virus (HSV) is an enveloped, double-stranded DNA virus of about 152 kbp, and has a natural tropism for neuronal and mucosal cells. HSV has been suggested to be of use both as a gene delivery vector in the nervous system and elsewhere and for the oncolytic treatment of cancer. In both applications the virus must however be disabled such that it is no longer pathogenic but such that it can still enter cells and perform the desired function. Thus for non-toxic gene delivery to target cells using HSV it has become apparent that in most cases immediate early gene expression must be prevented/minimized from the virus. For the oncolytic treatment of cancer, which may also include the delivery of gene(s) enhancing the therapeutic effect, a number of mutations to HSV have been identified which still allow the virus to replicate in culture or in actively dividing cells in vivo (e.g. in tumors), but which prevent significant replication in normal tissue. Such mutations include disruption of the genes encoding ICP34.5, ICP6 and thymidine kinase. Of these, viruses with mutations to ICP34.5, or ICP34.5 together with mutations of e.g. ICP6 have so far shown the most favorable safety profile. Viruses deleted for only ICP34.5 have been shown to replicate in many tumor cell types in vitro and to selectively replicate in artificially induced brain tumors in mice while sparing surrounding tissue. Early stage clinical trials have also shown their safety in man. Examples of such viruses and uses are described in PCT publications WO 2001/053506, WO 98/004726, WO 98/051809 and WO 99/060145.

In one embodiment, the oncolytic virus is an HSV1 virus. One exemplary oncolytic virus strain is HSV1 strain JS 1 deposited at the European Collection of Cell Cultures (ECACC), CAMR, Sailsbury, Wiltshire SP4 0JG, United Kingdom, on Jan. 2, 2001 under accession number 01010209. Oncolytic virus strains such as this may be modified as described herein to express galactosyl transferase enzymes for use in the methods provided.

iii) Vaccinia Virus

In one embodiment, the oncolytic virus is a vaccinia virus. Vaccinia virus is an enveloped, double-stranded DNA virus of about 200 kB. This virus replicates in the cytoplasm, bringing with its infectious particle the enzymes required for DNA replication and transcription of its genes. Vaccinia virus has many attributes that make it a good oncolytic virus. It has a large genome with the capacity to accommodate multiple foreign genes, it has a broad host range, it replicates rapidly, and it can easily be recombined for making viral mutants. A good safety record has been established through use of vaccinia virus as a smallpox vaccine.

iv) Measles Virus

In one embodiment, the virus is a measles virus (MeV) or a vaccine strain of MeV such as the Edmonston strain ($MeV_{Edm}$). MeV utilizes two envelope glycoproteins (the fusion protein (F) and the hemagglutinin protein (H)) to gain entry into the target cell. Protein F is a type I transmembrane protein, while protein H is a type II transmembrane domain, i.e. its amino-terminus is exposed directly to the cytoplasmic region. Both proteins thus comprise a transmembrane and a cytoplasmic region. One known function of the F protein is mediating the fusion of viral membranes with the cellular membranes of the host cell. Functions attributed to the H protein include recognizing the receptor on the target membrane and supporting F protein in its membrane fusion function. The direct and highly efficient membrane fusion at the cellular surface membrane is a particular property of measles virus and the morbilliviruses, thus distinguishing themselves from many other enveloped viruses that become endocytosed and will only fuse upon pH drop upon endocytosis. Both proteins are organized on the viral surface in a regular array of tightly packed spikes, H tetramers, and F trimers (Russell et al., Virology 199:160-168, 1994).

The Edmonston strain of MeV ($MeV_{Edm}$) uses a single protein as its main receptor, namely, the protein known to be the regulator of complement activation factor, CD46 (Gerlier et al., Trends Microbiol. 3:338-345, 1995). CD46 is expressed on all nucleated human cells. Most clinical isolates of measles virus, however, cannot effectively use CD46 as a receptor. Human SLAM (signaling lymphocyte-activation molecule; also known as CDw150) is a recently discovered membrane glycoprotein that is expressed on some T and B cells, and was also found to act as a cellular receptor for MeV, including the Edmonston strain (Tatsuo et al., Nature 406(6798):893-7, 2000). The precise biological functions and interactions of the MeV H and F proteins remain largely unclear.

There are a number of oncolytic viruses in clinical development for cancer that can be modified to include a hexosyl transferase encoding nucleic acid sequence such as alpha1, 3-galactosyltransferase. Examples of such oncolytic viruses include Ad-mda7 (p53 Inc), Ad-p53 (p53 Inc.), CG-0070 (Cold Genesys, Inc.), DNX-2401 (DNAtrix, Inc.), DWP-418 (Daewoong Pharmaceutical), HSV expressing huIL-12 (Univ. Alabama Birmingham), G-47 Delta (Univ. Tokyo Hospital), ganciclovir/ADV-TK (Shenzhen Tiandakang), GLONC-1 (Genelux Corp.), GLONC-2 (Genelux Corp.), GLONC-3 (Genelux Corp.), HF-10 (Takara Holdings), HSV-1716 (Virttu Biologics), JX-929 (Jennerex Bioterapeutics), KH-901 (Chengdu Kanghong Pharmaceuticals), MV-NIS Vaccine (Mayo Clinic), NDV-HUJ Oncolytic (Hadassah medical), OBP-301 (Oncolys BioPharma), Oncolytic AdV (Erasmus MC), ONCOS-102 (Oncos Therapeutics), ORCA-010 (Orca Therapeutics), Parvovirus H-1 (Oryx GmbH), pexastimogene devacirepvec (Jennerex Bioterapeutics), PV-701 (Wellstat Biologics), talimogene laherparepvec (Amgen), TG-1042 (Ascend Biopharmaceuticals), VCN-01 (VCN Biosciences), and VirRx-007 (p53 Inc.).

Viruses of the invention infect and replicate in tumor cells, subsequently killing the tumor cells. Thus, such viruses are replication competent. Preferably, they are selectively replication competent in tumor cells. This means that either they replicate in tumor cells and not in non-tumor cells, or that they replicate more effectively in tumor cells than in non-tumor cells. Cells in which the virus is able to replicate are permissive cells.

Measurement of selective replication competence can be carried out by the tests described herein for measurement of replication and tumor cell-killing capacity, and also analyzed by the statistical techniques mentioned herein if desired.

A virus of the invention preferably has a greater ability than an unmodified parent strain to infect or replicate in a tumor cell, to kill tumor cells or to spread between cells in tissues. Preferably this ability is a statistically significant greater ability. For example, a virus according to the invention may have up to 1.1 fold, 1.2 fold, 1.5 fold, 2 fold, 5 fold, 10 fold, 20 fold, 50 fold or 100 fold the capacity of the unmodified parent strain in respect of the property being tested.

The properties of the virus strain in respect of tumor cells can be measured in any manner known in the art. For example, the capacity of a virus to infect a tumor cell can be quantified by measuring the dose of virus required to infect a given percentage of cells, for example 50% or 80% of cells. The capacity to replicate in a tumor cell can be measured by growth measurements such as those carried out in the Examples, e.g. by measuring virus growth in cells over a period of 6, 12, 24, 36, 48 or 72 hours or longer. Similarly, the ability of a virus to lyse tumor cells can be quantified by measuring the proportion of living (versus dead) cells in cultures incubated with a given dose of virus over a period of 6, 12, 24, 36, 48 or 72 hours or longer.

B) Heterologous Nucleic Acid Sequences and Promoters

The viruses of the invention may be modified to carry heterologous nucleic acid sequences. In one embodiment, the heterologous nucleic acid encodes a hexosyl transferase. In one embodiment, the nucleic acid sequence encodes a galactosyl transferase. In one particular embodiment, the nucleic acid sequence encodes alpha 1,3-galactosyltransferase. The terms "α1,3-galactosyltransferase", "alpha-1,3-galactosyltransferase", "alpha1,3GT", "α1,3GT", "glycoprotein alpha-galactosyltransferase 1" and "GGTA1", as used herein refer to any enzyme capable of synthesizing alpha-gal epitopes. The enzyme is produced in most mammals with the exception of humans, apes and Old World monkeys. The carbohydrate structure produced by the enzyme is immunogenic in human and most healthy people have high titer natural anti alpha-gal antibodies, also referred to as "anti-Gal" antibodies. In some embodiments, the term "alpha 1,3GT" refers to a mouse alpha1,3GT (e.g., *Mus musculus*-nucleotides 460 to 1680 of GENBANK Accession No. NM_010283) and its gene product, as well as its functional mammalian counterparts (e.g., other New World monkeys, prosimians and non-primate mammals, but not Old World monkeys, apes and humans). In some embodiments, the term "alpha1,3GT" refers common marmoset gene (e.g., *Callithrix jacchus*—GENBANK Accession No. S71333), bovine alpha 1,3GT (e.g., *Bos taurus*—GENBANK Accession No. NM_177511), feline alpha1,3GT (e.g., *Felis catus*—GENBANK Accession No. NM_001009308), ovine alpha1,3GT (e.g., *Ovis aries*—GENBANK Accession No. NM_001009764), rat alpha1,3GT (e.g., *Rattus norvegicus*—GENBANK Accession No. NM_145674) and porcine alpha1,3GT (e.g., *Sus scofa*—GENBANK Accession No. NM_213810). Some embodiments of the present invention comprise a functional variant of a mammalian alpha1,3GT, which differs from the wild type mammalian alpha1,3GT sequences in, for example, fewer than 1-5% of the residues. In particular, alpha1,3GT variants include but are not limited to naturally occurring functional mammalian alpha1,3GT variants, as well as non-naturally occurring variants generated by recombinant or other means (e.g., 1, 2, 3, 4 or 5 amino acid substitutions, deletions, or additions, preferably corresponding to a residue from a functional mammalian alpha1,3GT homolog) are contemplated to find use in the compositions and methods of the present invention. In other embodiments, truncated forms of a mammalian alpha1,3GT, which retain catalytic activity, are employed (e.g., GGTA1 lacking 90 amino acid N-terminal stem region). However, deletion of 3 amino acids from the C-terminus of this enzyme results in its complete inactivation (Henion, T. R., B. A. Macher, F. Anaraki and U. Galili, Glycobiology 4:193-201, 1994).

Alpha1,3-galactosyltransferase has been previously engineered in adenovirus and used for cellular transfer (Deriy et al. Glycobiology, 12(2), 135-44 2002; Deriy et al. *Cancer Gene Therapy*, 12(6), 528-39, 2005). Alpha 1,3-galactosyltransferase has never been engineered to be expressed by oncolytic viruses for the combination lysis/immunization method described herein.

In the embodiments described herein, the heterologous nucleic acid sequence is preferably operably-linked to a control sequence permitting expression of said gene in a cell in vivo. Viruses of the invention may thus be used to deliver the heterologous nucleic acid sequences to a cell in vivo where it will be expressed.

According to a further aspect of the invention, there is provided a method of preparing the oncolytic virus as defined herein which comprises the step of incorporating a nucleic acid encoding a hexosyl transferase enzyme into the genome of said oncolytic virus.

The heterologous nucleic acid sequence may be inserted into the viral genome by any suitable technique such as homologous recombination of HSV strains with, for example, plasmid vectors carrying the gene flanked by HSV sequences.

The heterologous nucleic acid sequence may be introduced into a suitable plasmid vector comprising herpes viral sequences using cloning techniques well-known in the art. Thus, in one embodiment, said incorporating step comprises cloning. The heterologous nucleic acid sequence may be inserted into the viral genome at any location provided that oncolytic properties are still retained. Heterologous nucleic acid sequence may be inserted at multiple sites within the virus genome. For example, from 2 to 5 genes may be inserted into the genome.

The transcribed sequence of the heterologous nucleic acid sequence is preferably operably linked to a control sequence permitting expression of the gene in a tumor cell. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous nucleic acid sequence and a signal for termination of transcription. The promoter is selected from promoters which are functional in mammalian, preferably human tumor cells. The promoter may be derived from promoter sequences of eukaryotic genes. For example, the promoter may be derived from the genome of a cell in which expression of the heterologous gene is to occur, preferably a mammalian, preferably a human tumor cell. With respect to eukaryotic promoters, they may be promoters that function in a ubiquitous manner (such as promoters of beta-actin, tubulin) or, alternatively, in a tumor-specific manner. There may also be promoters that respond to specific stimuli, for example promoters that bind steroid hormone receptors. Viral promoters may also be used, for example the Moloney murine leukemia virus long terminal repeat (MMLV LTR) promoter or other retroviral promoters, the human or mouse cytomegalovirus (CMV) IE promoter, or promoters of herpes virus genes including those driving expression of the latency associated transcripts.

Expression cassettes and other suitable constructs comprising the heterologous nucleic acid sequence and control sequences can be made using routine cloning techniques known to persons skilled in the art (see, for example, Sambrook et al., 1989, Molecular Cloning—A laboratory manual; Cold Spring Harbor Press).

It may also be advantageous for the promoters to be inducible so that the levels of expression of the heterologous nucleic acid sequence can be regulated during the life-time of the tumor cell. Inducible means that the levels of expression obtained using the promoter can be regulated. For example, a virus of the invention may further comprise a heterologous nucleic acid sequence encoding the tet repressor/VP16 transcriptional activator fusion protein under the control of a strong promoter (e.g. the CMV IE promoter) and the heterologous nucleic acid sequence may be under the control of a promoter responsive to the tet repressor VP 16 transcriptional activator fusion protein previously reported (Gossen and Bujard, 1992, Gossen at al, 1995). Thus, in this example, expression of the heterologous nucleic acid sequence would depend on the presence or absence of tetracycline.

Multiple heterologous genes can be accommodated in the herpes virus genome. Therefore, a virus of the invention may comprise two or more heterologous nucleic acid sequences, for example from 2 to 3, 4 or 5 heterologous nucleic acid sequences. More than one gene and associated control sequences could be introduced into a particular oncolytic virus strain either at a single site or at multiple sites in the virus genome. Alternatively, pairs of promoters (the same or different promoters) facing in opposite orientations away from each other, each driving the expression of an heterologous nucleic acid sequence may be used.

In another embodiment, an immunomodulatory protein is co-expressed with the galacotsyl transferase enzyme. Preferably the immunomodulatory protein will enhance the anti-tumor activity of the virus. More preferably the protein is GM-CSF or another cytokine, a chemokine such as RANTES, or another immunomodulatory molecule such as B7.1, B7.2 or CD40L. Most preferably the immunomodulatory molecule is GM-CSF. Thus, in one embodiment, the oncolytic virus comprises a nucleic acid sequence encoding GM-CSF. The immunomodulatory gene may be any allelic variant of a wildtype gene, or it may be a mutant gene. The immunomodulatory gene will be derived from a mammal, preferably a rodent or primate, more preferably a human.

C) Pharmaceutical Compositions

Pharmaceutical compositions of the oncolytic viruses of the present invention can be formulated in any conventional manner using one or more physiologically acceptable carriers or excipients. The pharmaceutical compositions of the present invention can be formulated for a variety of modes of administration, including systemic, topical or localized administration. Techniques and formulations can be found in, for example, Remington's Pharmaceutical Sciences, Meade Publishing Co., Easton, Pa.

In one embodiment, the oncolytic virus composition is formulated for intravenous administration, intramuscular administration, intraperitoneal administration, intratumoral administration, subcutaneous administration, oral administration, rectal administration, intravaginal administration, intranasal administration, transmucosal administration or transdermal administration.

In a further embodiment, the oncolytic virus composition is formulated for intravenous administration, intramuscular administration, intraperitoneal administration, subcutaneous administration, oral administration, rectal administration, intravaginal administration, intranasal administration, transmucosal administration or transdermal administration.

The delivery of suitable oncolytic virus to cancerous cells that are to be treated may be performed using naked virus or by encapsulation of the virus in a carrier, e.g. in nanopartides, liposomes or other vesicles.

Administration is preferably in a "therapeutically effective amount", this being sufficient to show benefit to the individual. The actual amount administered, and rate and time-course of administration, will depend on the nature and severity of the tumor being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The oncolytic virus may be administered at any therapeutically effective dosage amount. Therapeutically effective dosages may be about, but not limited to, $10^3$, about $10^4$, about $10^5$, about $10^6$, about $10^7$, about $10^8$ or about $10^9$ plaque forming units (pfu).

For systemic administration, injection is preferred, including intratumoral, intramuscular, intravenous, intraperitoneal, and subcutaneous. For the purposes of injection, the pharmaceutical compositions of the present invention can be formulated in liquid solutions, preferably in physiologically compatible buffers, such as Hank's solution or Ringer's solution. In addition, the pharmaceutical compositions may be formulated in solid form and redissolved or suspended immediately prior to use. Lyophilized forms of the pharmaceutical composition are also suitable.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts, and fusidic acid derivatives. In addition, detergents may be used to facilitate permeation. Transmucosal administration can occur using nasal sprays or suppositories. For topical administration, the vector particles of the invention can be formulated into ointments, salves, gels, or creams as generally known in the art. A wash solution can also be used locally to treat an injury or inflammation in order to accelerate healing.

The pharmaceutical compositions can be formulated for parenteral administration by injection, e.g. by bolus injection or continuous infusion. Formulations for injection can be presented in a unit dosage form, e.g. in ampoules or in multi-dose containers, with an optionally added preservative. The pharmaceutical compositions can further be formulated as suspensions, solutions or emulsions in oily or aqueous vehicles, and may contain other agents including suspending, stabilizing and/or dispersing agents.

The invention also includes a kit comprising a pharmaceutical composition of the invention and a delivery device for delivering the composition to a subject. By way of example, the delivery device may be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit may further comprise an instructional material as described herein.

II) Methods

Virus compositions of the invention may be used in methods of cancer therapy of the human or animal body. In particular, viruses of the invention may be used in the oncolytic treatment of cancer, either with or without additional pro-drug therapy or stimulation of an anti-tumor immune response. Virus compositions of the invention may be used in the therapeutic treatment of any solid tumor in a mammal, preferably in a human.

Thus, according to a further aspect of the invention, there is provided a method of treating an individual with a neoplasm which comprises the steps of:
  i) expressing an endogenous enzyme delivered by the oncolytic virus as defined herein in at least one cancer cell to modify cell membrane glycosylation; and
  ii) inducing lysis of the at least one cancer cell resulting from administration of the oncolytic virus.

In one embodiment, the method is directed to treating an individual with cancer by administering an effective amount of an oncolytic virus composition wherein virus infection causes expression of hexosyl transferase prior to lysis.

In one embodiment, the oncolytic virus is administered in an effective amount to infect at least one cancer cell in the individual.

In another embodiment, alpha-gal epitopes are inserted into the infected cell membrane within 10 hours of infection.

In another embodiment, alpha-gal epitopes insert into the infected cell membrane prior to lysis of the infected cell.

In one embodiment, the method is directed to treating an individual with cancer.

In another embodiment, the method is directed to treating an individual with a tumor.

In another embodiment, the method is directed to treating an individual with cancer.

In one embodiment, the modified cell membrane actively targets membrane fragments for antigen presenting cell recruitment.

In another embodiment, the enzyme is sufficient to express alpha-gal epitopes on the infected cell membrane prior to lysis.

In another embodiment, alpha1,3-galactosyltransferase expression is sufficient to induce an effective immune response to the infected cell after lysis.

In another embodiment, the alpha-gal epitopes are sufficient to attract antigen-presenting cells to the tumor site.

In another embodiment, the enzyme is expressed within 4 hours from infection.

In another embodiment, the alpha-gal epitopes are sufficient to bind anti-gal antibodies in the tumor site.

Anti-Gal mediated destruction of tumors described in this method may be achieved by injection of gene therapy vectors containing the alpha1,3-galactosyltransferase gene. In one embodiment, the present invention contemplates a method of treating melanoma patients with multiple metastases comprising intratumoral injections of replication competent oncolytic virus containing the alpha1,3-galactosyltransferase gene. In one embodiment intratumoral injection of viral compositions results in transduced tumor cells expressing alpha-gal epitopes, wherein these tumor cells induce intratumoral inflammation prior to lysis. Intratumoral inflammation recruits antigen presenting cells such as dendritic cells, macrophages and certain B-cells. Infected cells can be either lysed by the engineered replication competent virus compositions described herein, or alternatively destroyed by the natural anti-Gal antibody bound to alpha-gal epitopes on the transduced cells via the complement dependent cytolysis (CDC) or antibody dependent cell mediated cytolysis (ADCC) mechanisms. Although it is not necessary to understand the mechanism of an invention, it is believed that the anti-Gal opsonized tumor membranes will actively target tumor cell membrane fragments or intact tumor cells to antigen presenting cells and thus, promote protective anti-tumor immunity.

In another embodiment, the present invention contemplates a method of treating colorectal carcinoma patients having multiple metastases in the colon and in the liver comprising intratumoral injections of oncolytic virus containing the alpha 1,3-galactosyltransferase gene. In one embodiment, the injection comprises colonoscopy or laparoscopy as means of delivering the viral vector into the tumor lesions.

In yet another embodiment, the present invention contemplates a method of treating lung carcinoma patients having multiple metastases in the lungs comprising intratumoral injections of oncolytic virus containing the alpha 1,3-galactosyltransferase gene. In one embodiment, the injection comprises bronchoscopy.

In another embodiment, the present invention contemplates a method of treating patients with urinary bladder carcinoma comprising an oncolytic virus containing the alpha 1,3-galactosyltransferase gene viral vector. In one embodiment, the vector is administered by means of cystoscopy.

In another embodiment, the present invention contemplates a method of treating patients with pancreatic adenocarcinoma comprising an oncolytic virus containing the alpha 1,3-galactosyltransferase gene viral vector. In one embodiment, the vector is administered by means of endoscopy or laparoscopy.

In another embodiment, the present invention contemplates a method of treating patients with mammary carcinoma comprising an oncolytic virus containing the alpha 1,3-galactosyltransferase gene viral vector. In one embodiment, the vector is administered by direct injection into the tumor.

Administration of an oncolytic virus containing the alpha 1,3-galactosyltransferase gene viral vector can be performed in any solid tumor or lymphoma that is accessible to intratumoral delivery of the alpha 1,3galactosyltransferase gene. For example, intratumoral delivery is described in U.S. Pat. No. 7,820,628.

Alternative methods to deliver the alpha 1,3-galactosyltransferase gene can be performed also with any type of viral and non-viral vector which can deliver genes. For example, these methods include, but are not limited to adenovirus vector, adenovirus helper virus, retrovirus vector, lentivirus vector, naked DNA vectors, herpes virus or naked RNA vectors or DNA vectors.

In another embodiment, the present invention contemplates a method to administer vectors containing the alpha 1,3-galactosyltransferase gene by injection into melanoma lesions or any other tumor lesion, whereby the epitopes insert into the tumor cell membranes. As in the case of tumor cells transduced with oncolytic virus containing the alpha 1,3-galactosyltransferase gene, the anti-Gal IgG will bind to the tumor cell membranes expressing alpha-gal epitopes and will target them to antigen presenting cells for eliciting a systemic immune response also against non-treated tumor lesions that express the tumor antigens. One of skill in the art should recognize that the present invention contemplates generation of adaptive anti-tumor immunity, driven by targeting by the anti-Gal antibody to antigen presenting cells by any composition introduced into the tumor mass that results in the in situ binding of this natural antibody to the tumor cells.

A) Administration

The viruses of the invention may be used in a patient, preferably a human patient, in need of treatment. A patient in need of treatment is an individual suffering from cancer, preferably an individual with a solid tumor. The aim of therapeutic treatment is to improve the condition of a patient. Typically, therapeutic treatment using a virus of the invention alleviates the symptoms of the cancer.

According to a further aspect of the invention, there is provided a method of treating cancer comprising administering a therapeutically effective amount of a virus of the invention to a patient suffering from cancer or having a neoplasm or tumor in need of treatment.

According to a further aspect of the invention, there is provided an oncolytic virus as defined herein or a pharmaceutical composition as defined herein for use in the treatment of cancer.

Administration of an oncolytic virus of the invention to an individual suffering from a tumor will typically kill the cells of the tumor thus decreasing the size of the tumor and/or preventing spread of malignant cells from the tumor while also recruiting antigen presenting cells (APCs) to the tumor site and inducing a protective anti-tumor immune response.

One method of administering therapy involves combining the virus with a pharmaceutically acceptable carrier or diluent to produce a pharmaceutical composition.

Suitable carriers and diluents include isotonic saline solutions, for example phosphate-buffered saline. The compositions described herein can be administered using conventional administration routes to promote viral infection at a tumor site.

In one embodiment, the compositions are administered via injection (for example intraperitoneal, intramuscular, intravenous, subcutaneous), inhalation or insulation (for example either through the mouth or the nose transmucosally or intranasally) or by oral, buccal, parenteral or rectal administration routes.

In one embodiment, the composition is administered by direct injection into target tissue which may be the tumor or a blood vessel supplying the tumor. The amount of virus administered is in the case of HSV in the range of from $10^4$ to $10^{10}$ plaque forming units (pfu), preferably from $10^5$ to $10^8$ pfu, more preferably about $10^6$ to $10^8$ pfu. Typically, up to 500μl, typically from 1 to 200μl preferably from 1 to 10μl of a pharmaceutical composition of the virus and a pharmaceutically acceptable suitable carrier or diluent would be used for injection. However, for some oncolytic therapy applications larger volumes up to, but not limited to 10 ml may also be used, depending on the tumor and the inoculation site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. The dosage and dosage frequency may first be optimized pre-clinically by studying the properties of the virus in tissue culture and in a suitable animal model.

The virus may be combined with a pharmaceutically acceptable carrier or diluent to produce a pharmaceutical composition. A suitable carrier for most viruses would be a buffered saline solution, such as phosphate buffered saline (PBS). The pharmaceutical composition will ideally be formulated to enable administration of the appropriate dose of virus in a volume of up to 1 ml, although there may be cases where up to a 10 ml volume is administered. In cases where individual tumor lesion volumes are deemed too small to be treated with the optimal dose, it is possible that the optimal dose is administered by treatment of multiple lesions, each administered with a fraction of the total optimal dose. It is also envisaged that multiple doses may be required to elicit an effective anti-tumor response. The dose interval may be determined based on efficacy data obtained in preclinical models or from clinical experience obtained with a similar virus strain.

Preferably the virus is administered by direct injection into the tumor. The virus may also be administered systemically or by injection into a blood vessel supplying the tumor. The virus may also be administered as an intravesical treatment; such as might be used for treatment of cancers of the bladder. The optimum route of administration will depend on the location and size of the tumor.

In one embodiment, the method is a method of treating an individual having a neoplasm comprising administering an effective amount of a modified oncolytic virus comprising a nucleic acid encoding a galactosyl transferase enzyme.

Thus, the oncolytic viruses of the present invention may be formulated for administration by, for example, injection, inhalation or insulation (either through the mouth or the nose) or by oral, buccal, parenteral or rectal administration.

B) Indications

In specific embodiments, the oncolytic viruses useful in the present methods may be administered to a subject with prostate, breast, lung, liver, endometrial, bladder, colon or cervical carcinoma; adenocarcinoma; melanoma; lymphoma; glioma; or sarcomas such as soft tissue and bone sarcomas.

In a further embodiment the invention is directed to the engineered oncolytic virus of the invention for the treatment or prevention of cancer, including, but not limited to, neoplasms, tumors, metastases, or any disease or disorder characterized by uncontrolled cell growth, and particularly multidrug resistant forms thereof. The cancer can be a multifocal tumor. Examples of types of cancer and proliferative disorders to be treated with the therapeutics of the invention include, but are not limited to, leukemia (e.g. myeloblastic, promyelocytic, myelomonocytic, monocytic, erythroleukemia, chronic myelocytic (granulocytic) leukemia, and chronic lymphocytic leukemia), lymphoma (e.g. Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. In a particular embodiment, therapeutic compounds of the invention are administered to patients having prostate cancer (e.g., prostatitis, benign prostatic hypertrophy, benign prostatic hyperplasia (BPH), prostatic paraganglioma, prostate adenocarcinoma, prostatic intraepithelial neoplasia, prostato-rectal fistulas, and atypical prostatic stromal lesions). In an especially preferred embodiment the medicaments of the present invention are used for the treatment of cancer, glioma, liver carcinoma and/or colon carcinoma. The treatment and/or prevention of cancer includes, but is not limited to, alleviating symptoms associated with cancer, the inhibition of the progression of cancer, the promotion of the regression of cancer, and the promotion of the immune response.

As used herein, the term neoplasm refers to an abnormal growth of tissue. A neoplasm may be benign or malignant. Generally, a malignant neoplasm is referred to as a cancer. Cancers differ from benign neoplasms in the ability of malignant cells to invade other tissues, either by direct growth into adjacent tissue through invasion or by implantation into distant sites by metastasis (i.e., transport through the blood or lymphatic system).

The methods of the present invention are suitable for the treatment of benign and malignant neoplasms (cancer).

As defined herein a superficial neoplasm is one located on the outer surface of the body that has confined itself and not spread to surrounding tissues or other parts of the body. An internal neoplasms located on an internal organ or other internal part of the body. An invasive neoplasm is a neoplasm that has started to break through normal tissue barriers and invade surrounding areas, e.g., an invasive breast cancer that has spread beyond the ducts and lobules.

A non-exclusive list of the types of neoplasms contemplated for treatment by the method disclosed herein includes the following categories: (a) abdominal neoplasms including peritoneal neoplasms and retroperitoneal neoplasms; (b) bone neoplasms including femoral neoplasms, skull neoplasms, jaw neoplasms, manibular neoplasms, maxillary neoplasms, palatal neoplasms, nose neoplasms, orbital neoplasms, skull base neoplasms, and spinal neoplasms; c) breast neoplasms including male breast neoplasms, breast ductal carcinoma, and phyllodes tumor; (d) digestive system neoplasms including biliary tract neoplasms, bile duct neoplasms, common bile duct neoplasms, gall bladder neoplasms, gastrointestinal neoplasms, esophegeal neoplasms, intestinal neoplasms, cecal neoplasms, appendiceal neoplasms, colorectal neoplasms, colorectal adenomatous polyposis coli, colorectal Gardner Syndrome, colonic neoplasms, colonic adenomatous polyposis coli, colonic Gardner Syndrome, sigmoid neoplasms, hereditary nonpolyposis colorectal neoplasms, rectal neoplasms, anus neoplasms, duodenal neoplasms, ileal neoplasms, jejunal neoplasms, stomach neoplasms, liver neoplasms, liver cell adenoma, hepatocellular carcinoma, pancreatic neoplasms, islet cell adenoma, insulinoma, islet cell carcinoma, gastrinoma, glucagonoma, somatostatinoma, vipoma, pancreatic ductal carcinoma, and peritoneal neoplasms; (e) endocrine gland neoplasms including adrenal gland neoplasms, adrenal cortex neoplasms, adrenocortical adenoma, adrenocortical carcinoma, multiple endocrine neoplasia, multiple endocrine neoplasia type 1, multiple endocrine neoplasia type 2a, multiple endocrine neoplasia type 2b, ovarian neoplasms, granulosa cell tumor, luteoma, Meigs' Syndrome, ovarian Sertoli-Leydig cell tumor, thecoma, pancreatic neoplasms, paraneoplastic endocrine syndromes, parathyroid neoplasms, pituitary neoplasms, Nelson Syndrome, testicular neoplasms, testicular Sertoli-Leydig cell tumor, and thyroid neoplasms (f) eye neoplasms including conjunctival neoplasms, orbital neoplasms, retinal neoplasms, retinoblastoma, uveal neoplasms, choroid neoplasms, and iris neoplasms; (g) brain, head and neck neoplasms including esophageal neoplasms, facial neoplasms, eyelid neoplasms, mouth neoplasms, gingival neoplasms, oral leukoplakia, hairy leukoplakia, lip neoplasms, palatal neoplasms, salivary gland neoplasms, parotid neoplasms, sublingual gland neoplasms, submandibular gland neoplasms, tongue neoplasms, otorhinolaryngologic neoplasms, ear neoplasms, laryngeal neoplasms, nose neoplasms, paranasal sinus neoplasms, maxillary sinus neoplasms, pharyngeal neoplasms, hypopharyngeal neoplasms, nasopharyngeal neoplasms, nasopharyngeal neoplasms, oropharyngeal neoplasms, tonsillar neoplasms, parathyroid neoplasms, thyroid neoplasms, and tracheal neoplasms; (h) hematologic neoplasms including bone marrow neoplasms; (i) nervous system neoplasms including central nervous system neoplasms, brain neoplasms, cerebral ventricle neoplasms, choroid plexus neoplasms, choroid plexus papilloma, infratentorial neoplasms, brain stem neoplasms, cerebellar neoplasms, neurocytoma, pinealoma, supratentorial neoplasms, hypothalamic neoplasms, pituitary neoplasms, Nelson Syndrome, cranial nerve neoplasms, optic nerve neoplasms, optic nerve glioma, acoustic neuroma, neurofibromatosis 2, nervous system paraneoplastic syndromes, Lambert-Eaton myasthenic syndrome, limbic encephalitis, transverse myelitis, paraneoplastic cerebellar degeneration, paraneoplastic polyneuropathy, peripheral nervous system neoplasms, cranial nerve neoplasms, acoustic neuroma, and optic nerve neoplasms; (j) pelvic neoplasms; (k) skin neoplasms including acanthoma, sebaceous gland neoplasms, sweat gland neoplasms and basal cell carcinoma; (l) soft tissue neoplasms including muscle neoplasms and vascular neoplasms; (m) splenic neoplasms; (n) thoracic neoplasms including heart neoplasms, mediastinal neoplasms, respiratory tract neoplasms, bronchial neoplasms, lung neoplasms, bronchogenic carcinoma, non-small-cell lung carcinoma, pulmonary coin lesion, Pancoasts's Syndrome, pulmonary blastoma, pulmonary sclerosing hemangioma, pleural neoplasms, malignant pleural effusion, tracheal neoplasms, thymus neoplasms, and thymoma; (o) urogenital neoplasms including female genital neoplasms, fallopian tube neoplasms, uterine neoplasms, cervix neoplasms, endometrial neoplasms, endometrioid carcinoma, endometrial stromal tumors, endometrial stromal sarcoma, vaginal neoplasms, vulvar neoplasms, male genital neoplasms, penile neoplasms, prostatic neoplasms, testicular neoplasms, urologic neoplasms, bladder neoplasms, kidney neoplasms, renal cell carcinoma, nephroblastoma, Deriys-Drash Syndrome, WAGR Syndrome, mesoblastic nephroma, ureteral neoplasms and urethral neoplasms; (p) and additional cancers including renal carcinoma, lung cancer, melanoma, leukemia, Barrett's esophagus, metaplasia pre-cancer cells.

The pharmaceutical compositions of the present invention can be administered alone or in combination with other types of cancer treatment strategies (e.g., radiation therapy, chemotherapy, hormonal therapy, immunotherapy and anti-tumor agents). Examples of anti-tumor agents include, but are not limited to, cisplatin, ifosfamide, paclitaxel, taxanes, topoisomerase I inhibitors (e. g., CPT-11, topotecan, 9-AC, and GG-211), gemcitabine, vinorelbine, oxaliplatin, 5-fluo-rouracil (5-FU), leucovorin, vinorelbine, temodal, and taxo.

The following non-limiting examples are provided to further illustrate the invention.

Example 1: Description of Preliminary Studies for Expression of Alpha-Gal Epitopes on Tumor Cells by Transduction with an Adenovirus Vector Containing the α1,3GT Gene Induction of expression of alpha-gal epitopes (Gal-alpha1-3Gal-beta1-4GlcNAc-R) on human tumor cells was previously studied by transduction with replication defective adenovirus vector that contains the α1,3GT gene as detailed in Deriy et al. Glycobiology 2002, 12: 135-144. For this purpose, the open reading frame (ORF) of the mouse alpha 1,3GT cDNA was inserted into a replication defective adenovirus vector, in which the early genes E1 and E3 genes were deleted. This was achieved by the use of the pAd shuttle plasmid containing the alpha 1,3GT cDNA that allows for homologous recombination of the cDNA into the replication defective adenovirus vector. In this plasmid, the α1,3GT gene was inserted downstream of the cytomegalovirus (CMV) promoter which is a very effective promoter in mammalian cells. The generated adenovirus vector containing the inserted mouse α1,3GT gene under the CMV promoter was propagated in the human kidney cell line 293 (ATCC) which contains the E1 complementing viral gene. The viral clone isolated was assayed for presence of α1,3GT cDNA that produces catalytically active enzyme, by transduction of 293 cells and analysis of alpha-gal epitope expression after 24 h by flow cytometry following *Bandeiraea simplicifolia* IB4 (BS lectin) binding. The BS lectin binds specifically to alpha-gal epitopes.

The replication defective adenovirus contacting the α1,3GT gene was designated AdαGT and was further propagated in the 293 cell line which contains the E1 complementing viral gene. The concentration of AdαGT was determined as multiplicity of infection (MOI) units and defined as the highest dilution of adenovirus vector that displayed cytopathic effects in 293 cells, 6 days post infection. The ability of AdαGT to induce synthesis and expression of alpha-gal epitopes on human tumor cells was studied with the human cervical carcinoma HeLa cell line, which like other malignant or normal human cells, it lacks alpha-gal epitopes.

Figure 3:
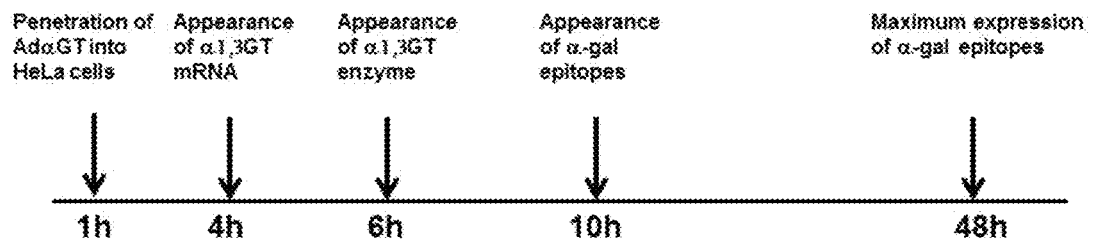
FIG. 3: Provides a schematic timeline for appearance of alpha-1,3 galactosytransferase ($\alpha$1,3GT) and alpha-gal epitopes in HeLa cells transduced by adenovirus containing the $\alpha$1,3GT gene (Ad$\alpha$GT).
Figure 4:
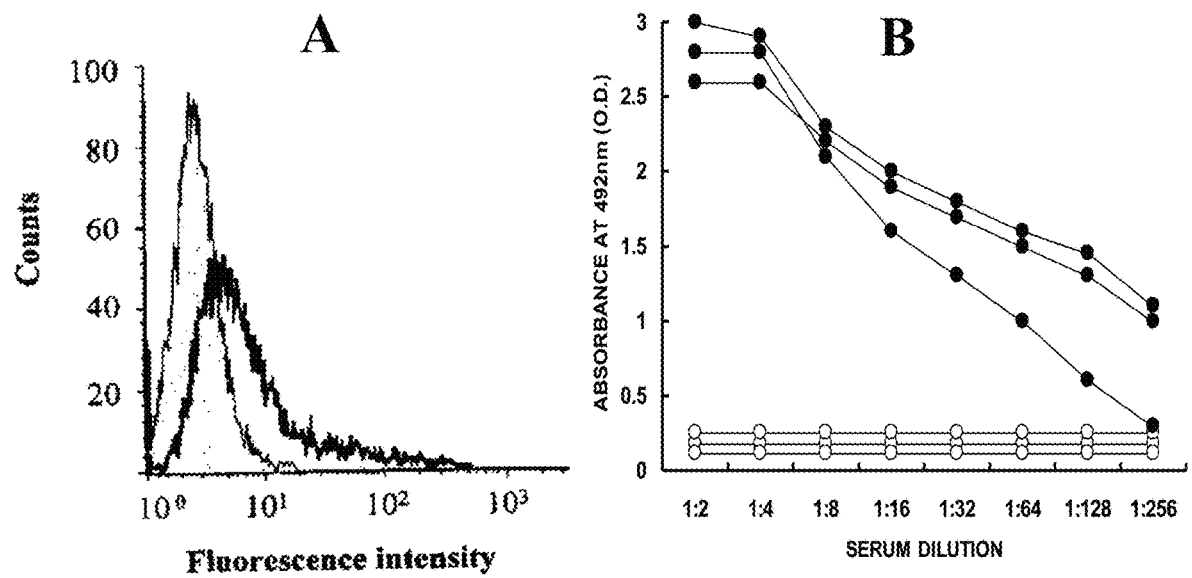
FIG. 4: Provides a graph showing expression of alpha-gal epitopes on mouse B16 melanoma cells transduced with Ad$\alpha$GT, as indicated by binding of Bandeiraea simplicifolia IB4 (BS) lectin (A) and mouse anti-Gal IgG (B). A. Expression of alpha-gal epitopes on $B16_{Ad\alpha GT}$ cells (i.e. B16 cells transduced by Ad$\alpha$GT [1×10 infectious units (IU)/ml]), as measured by flow cytometry of cells stained with BS lectin. The lectin is coupled to fluorescein (FITC). Thin line histogram with dotted area-$B16_{Adcont}$ cells (i.e. melanoma cells transduced with adenovirus containing no inserted genes); thick line histogram-$B16_{Ad\alpha GT}$ cells. B. Binding of anti-Gal in alpha 1,3-galactosyltransferase knockout mouse serum to alpha-gal epitopes on $BL6_{Ad\alpha GT}$ cells (●), or on $B16_{Adcont}$ cells (○), as determined by ELISA. Data are of 3 representative mice out of 6 mice with similar results.
Figure 5:
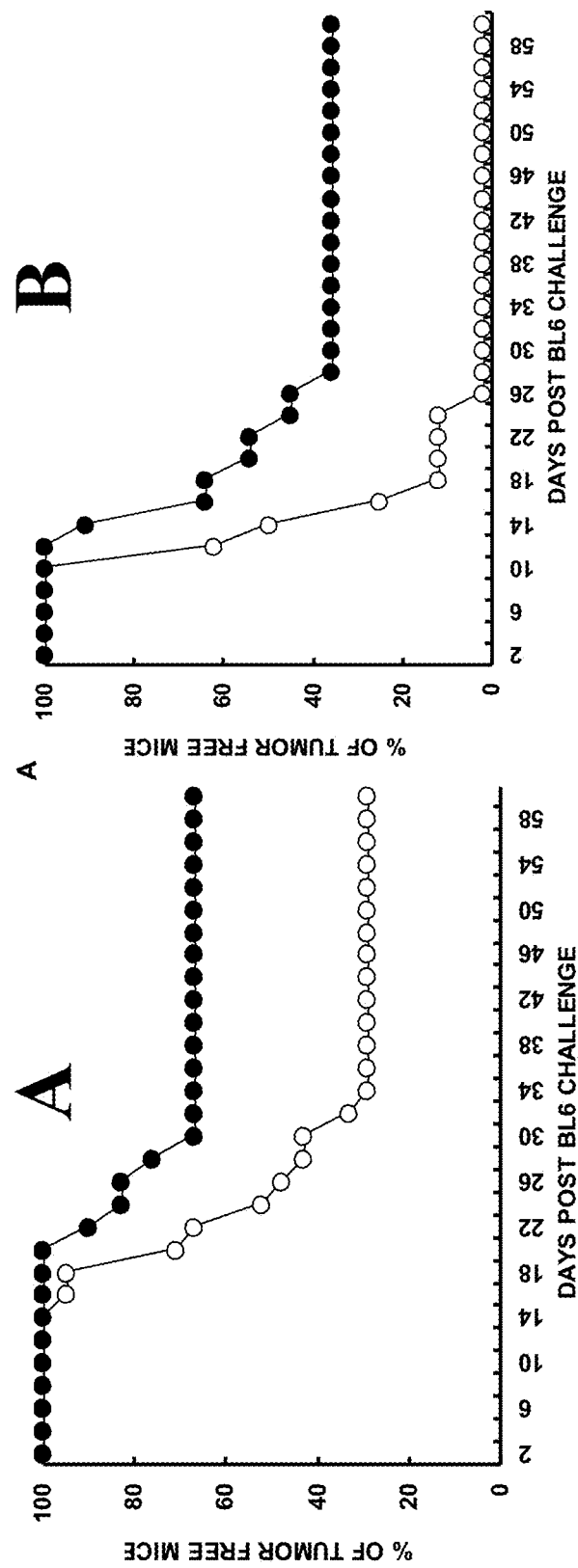
FIG. 5: Provides a graph showing protection of alpha 1,3-galactosyltransferase knockout mice from B16 tumor challenge using $B16_{Ad\alpha GT}$ vaccine. Alpha 1,3-galactosyltransferase knockout mice producing anti-Gal were vaccinated with 2×10$^6$ irradiated B16 cells expressing alpha-gal epitopes ($B16_{Ad\alpha GT}$)(●), or with irradiated B16 cells transduced with control adenovirus ($B16_{Adcont}$) (○). This immunization was repeated after one week. The mice were challenged, one week later, with 0.2×10$^6$ live B16 cells (A), or 0.5×10$^6$ live B16 cells (B). Mice were monitored every day for 2 months for tumor growth. Results are presented as percentage of mice remaining tumor-free at various days post tumor challenge. Results are of 22 mice in the experimental group and 21 in the control group in (A) and in separate experiment of 21 mice in the experimental group and 18 in the control group in (B).

Transduction of HeLa cells resulted in immediate penetration of ~20 AdαGT copies into each cell. The appearance of α1,3GT mRNA originating from AdαGT was determined by reverse transcriptase polymerase chain reaction (RT-PCR) using upstream and downstream primers specific to the mouse α1,3GT gene (5'-ATGAATGTCAAGG-GAAAAG-3' (SEQ ID NO: 1) and 3'-TCAGACATTAT-TTCTAACCA-5' (SEQ ID NO: 2)). Based on this analysis α1,3GT mRNA was found in the cytoplasm of the HeLa cells, 4 h after transduction. The actual appearance of the α1,3GT enzyme in the cytoplasm was determined by the catalytic activity of this enzyme. α1,3GT transfers galactose from the sugar donor UDP-Gal to nine terminal N-acetyllactosamine residues on N-linked carbohydrate chains of the protein asialofetuin coating ELISA wells. De novo synthesized alpha-gal epitopes were identified by ELISA with the monocional anti-Gal antibody M86 (Galili et al. Transplantation, 65:1129-1132, 1998). By using this assay, catalytic activity of α1,3GT was first detected in the transduced HeLa cells after 6 h (see timeline in FIG. 3). The initial appearance of α-gal epitopes was detected by a sensitive monoclonal anti-Gal M86 antibody binding assay called ELISA Inhibition Assay which measures the number of alpha-gal epitopes per cell (Galili et al, supra). By using this assay expression of alpha-gal epitopes on HeLa cell surface glycoconjugates was detected 10 h post transduction at a level of $6 \times 10^4$/cell. Within 48 h post transduction the number of expressed alpha-gal epitopes increased to $2 \times 10^6$ epitopes/cell. (FIG. 3).

Since AdαGT is replication defective and cannot proliferate in dividing cells, each cell division of the transduced HeLa cells results in the decrease in the number of α1,3GT copies by 50%. Accordingly, expression of alpha-gal epitopes decreases on the surface of the cells so that within 2 weeks post transduction no alpha-gal epitopes are detected on the cells and no α1,3GT gene is detected within the cells.

Example 2: Expression of Alpha-Gal Epitopes on B16-BL6 Melanoma Cells Transduced with Adenovirus Vector Containing the Alpha 1,3-Galactosyltransferase Gene In order to achieve introduction of the alpha 1,3-galactosyltransferase gene into cells, this gene was inserted into a replication incompetent adenovirus vector as previously described (Deriy et al. Glycobiology 2002, 12: 135). The resulting vector is designated AdαGT and is very effective in inducing expression of alpha-gal epitopes on human tumor cells (Deriy L et al, supra). The expression of alpha-gal epitopes was determined on AdαGT transduced B16-BL6 melanoma cells. These cells are a subclone of B16 melanoma and are referred to as BL6 cells. The transduction of BL6 cells with AdαGT results in intracellular production of alpha 1,3-galactosyltransferase that is encoded by the alpha 1,3-galactosyltransferase gene within the transducing AdαGT. The de novo expression of alpha-gal epitopes on cell surface glycoconjugates following synthesis of this epitope by the alpha 1,3-galactosyltransferase was evaluated 48 hour post transduction. Alpha-gal epitopes were detected by the binding of *Bandeiraea* (*Griffonia*) *simplicifolia* IB4 lectin (BS lectin—a lectin specific to α-gal epitopes) as measured by flow cytometry and by the binding of the anti-Gal antibody to the transduced cells as measured by ELISA. BL6 cells transduced with AdαGT (referred to as $BL6_{AdαGT}$ cells) displayed a significant shift following BS lectin binding, as measured by flow cytometry, in comparison to B16 cells transduced with the control "empty" adenovirus that lacks the alpha1,3-galactosyltransferase gene insert (referred to as $BL6_{Adcont}$ cells) (FIG. 4A). In addition, ~15% of the $BL6_{AdαGT}$ cells displayed a much higher degree of lectin binding than the rest of the population, indicating that these cells express alpha-gal epitopes in high numbers of epitopes per cell.

The ability of mouse anti-Gal IgG to bind to the alpha-gal epitopes on $BL6_{AdαGT}$ cells was demonstrated by ELISA (FIG. 4B). The $BL6_{cont}$ cells or $BL6_{AdαGT}$ cells were attached to ELISA wells by drying. Subsequently, serum containing anti-Gal IgG was added at serial twofold dilutions to the wells and anti-Gal IgG binding determined by the binding of horseradish peroxidase (HRP) conjugated goat anti-mouse IgG antibody. Nonspecific IgG binding values were subtracted by parallel measurement of IgG binding to wells coated with non-transduced BL6 cells. Anti-Gal readily bound to $BL6_{AdαGT}$ cells even at serum dilution of 1:128, whereas no binding was observed in wells coated with $BL6_{Adcont}$ can cells in any of the serum dilutions (FIG. 4B).

Example 3: Efficacy of $BL6_{AdαGT}$ Cells in Eliciting a Protective Anti-Tumor Immune Response The efficacy of AdαGT transduced tumor cells as vaccines was studied in alpha 1,3-galactosyltransferase knockout mice, as detailed in Deriy et al. Cancer Gene Therapy 12: 528-539, 2005). The B16-BL6 cells served as the tumor model. Anti-Gal producing mice were vaccinated with $2 \times 10^6$ irradiated $BL6_{AdαGT}$ cells, or with $2 \times 10^6$ irradiated BL6 cells that were transduced with the control parental adenovirus vector lacking the alpha 1,3-galactosyltransferase gene. The latter cells, referred to as $BL6_{Adcont}$, did not express alpha-gal epitopes and served for immunization of the control mice. The immunization was repeated after one week. One week after the second immunization, the mice were challenged subcutaneously with $0.2 \times 10^6$ or $0.5 \times 10^6$ live BL6 cells. Tumor development was monitored for 2 months. Two thirds of the mice immunized with $BL6_{AdαGT}$ cells and challenged with $0.2 \times 10^0$ non-transduced parental BL6 cells were protected against the challenge, whereas only 20% of the control group did not develop tumor (FIG. 5A). When the mice were challenged with the higher dose of $0.5 \times 10^6$ live BL6 cells, one third of the mice immunized with $BL6_{AdαGT}$ cells developed protection against the tumor challenge, whereas all control mice vaccinated with BL6 cells transduced with the control virus $Ad_{cont}$, developed tumors within 25 days post challenge with BL6 cells (FIG. 5B). These results imply that AdαGT transduced tumor cells expressing alpha-gal epitopes can serve as tumor vaccines that are effectively targeted to antigen presenting cells and thus, can induce an immune response against the same tumor cells, which lack alpha-gal epitopes.

Example 4: Kinetics of Alpha-Gal Epitope Expression Vs. Cytolysis in Tumor Cells Infected with Herpes Virus Containing the α1,3GT Gene ($HSV_{αGT}$)

The objective of this experiment is to determine in vitro the timeline for the expression of alpha-gal epitopes on human and mouse tumor cells following the infection of the cells with oncolytic herpes virus containing the α1,3GT gene ($HSV_{αGT}$). This analysis is required in order to confirm that the expression of alpha-gal epitopes on infected cells occurs prior to the cytolysis of the cells by this oncolytic virus. It is assumed that once the alpha-gal epitopes are expressed on cell membranes they will bind the natural anti-Gal antibody even after the cells are lysed by the oncolytic virus $HSV_{αGT}$. The immune complexes formed between anti-Gal and fragmented tumor cell membranes (because of the cell lysis) will be effectively targeted for uptake by APCs such as dendritic cells and macrophages, as a result of the interaction between the Fc portion of the immunocomplexed anti-Gal antibody and Fcγ receptors (FcγR) on APC (see FIGS. 1 and 2). In order to prepare $HSV_{αGT}$, the α1,3GT gene under the CMV promoter is amplified by PCR from the replication defective virus AdαGT described above and in (Deriy et al 2002, supra).

The gene under CMV promoter is inserted into an oncolytic HSV and suspensions of the resulting $HSV_{\alpha GT}$ are prepared by propagation in HeLa cells according to methods known to those skilled in the art.

The expression of alpha-gal epitopes is determined on $HSV_{\alpha GT}$ infected B16F10 (B16) mouse melanoma cells and on human HeLa cervical carcinoma cells. The study with the mouse melanoma cells is required to determine the subsequent feasibility of the in vivo study with these cells in mice. The B16 melanoma is the only known mouse tumor cell line that lacks alpha-gal epitopes and thus it simulates human tumor cells in the lack of this carbohydrate epitope. The study with the HeLa cells is required to confirm that the assumption that alpha-gal epitope expression in $HSV_{\alpha GT}$ infected human tumor cells occurs prior to the cytolysis of the cells by this virus. The study is described for B16 cells, but is identical also for the HeLa cells.

A suspension of $HSV_{\alpha GT}$ virus is added to monolayers of B16 cells at a concentration of $1\times10^6$-$2\times10^7$ pfu (plaque forming units)/ml. The infected cells are detached every 2 hours and the expression of the α1,3GT gene of the virus is determined by the appearance of α1,3GT mRNA. This mRNA is detected by reverse transcriptase polymerase chain reaction (RT-PCR) using upstream and downstream primers specific to the mouse α1,3GT gene (5'-ATGAATGT-CAAGGGAAAAG-3' (SEQ ID NO: 1) and 3'-TCAGACAT-TATTTCTAACCA-5' (SEQ ID NO: 2)) as described for AdαGT above. The actual appearance of the α1,3GT enzyme in the cytoplasm of the infected cells is determined by the catalytic activity of this enzyme in ELISA using asialofetuin as an acceptor for the enzyme and UDP-Gal is used as the sugar donor. Asialofetuin further functions as a solid phase antigen coating ELISA wells. De novo synthesized alpha-gal epitopes are identified by ELISA with the monoclonal anti-Gal antibody M86 (Galili, 1998, supra). The subsequent appearance of alpha-gal epitopes is detected by the binding of *Bandeiraea* (*Griffonia*) *simplicifolia* IB4 lectin (BS lectin—a lectin specific to alpha-gal epitopes) as measured by flow cytometry and by the binding of the anti-Gal antibody to the infected cells processed to coat ELISA by drying the cells in ELISA wells. The alpha-gal epitope expression is further quantified by the sensitive monoclonal anti-Gal M86 antibody binding assay called ELISA Inhibition Assay which measures the number of alpha-gal epitopes per cell (Galili et al. 1998, supra). An "empty" HSV (i.e. virus lacking the α1,3GT gene) is used as a control for the viral infection.

The cell cultures continue to be monitored microscopically for cytolysis in order to determine the period post infection in which the cells undergo cytolysis.

Example 5: Efficacy of $HSV_{\alpha GT}$ or as an In Situ Oncolytic Virus

The efficacy of $HSV_{\alpha GT}$ as an oncolytic virus and as means to generate protective anti-tumor immunity against various tumor associated antigens (TAA) is determined according to the studies (Galili et al. J Immunol.; 178: 4676-87, 2007; Abdel-Motal et al. Cancer Immunol Immunother.; 58: 1545-55, 2009.) These studies are performed in alpha 1,3-galactosyltransferase knockout mice producing the anti-Gal antibody. The B16 cells serve as the tumor model. Anti-Gal producing alpha1,3-galactosyltransferase knockout mice are injected subcutaneously in the right abdominal flank with $1\times10^6$ B16 cells. As a result of this injection the B16 cells develop into a melanoma tumor lesion with a diameter of 4-5 mm within 5-6 days. $HSV_{\alpha GT}$ at an amount ranging between $10^3$-$10^6$ pfu in a volume of 0.1 ml is injected into the tumors. Oncolytic HSV lacking the inserted α1,3GT gene ("empty" HSV) is used as control virus incapable of inducing the expression of α-gal epitopes. The mice are monitored for 2 months for the disappearance of the tumor lesion. Mice with tumors reaching the diameter of 20 mm are euthanized. The amount of $HSV_{\alpha GT}$ which is twice the amount displaying complete elimination of the tumor (i.e. 100% oncolysis) is determined and used for further studies evaluating the protective anti-tumor immune response elicited by this treatment.

Comparison with the control HSV lacking the α1,3GT gene determines whether $HSV_{GT}$a is more, or less effective than the control virus in inducing oncolysis.

Example 6: Efficacy of $HSV_{\alpha GT}$ Infected Lesions in Eliciting a Protective Anti-Tumor Immune Response Against Distant Metastases Anti-Gal producing alpha1,3-galactosyltransferase knockout mice are injected subcutaneously in the right abdominal flank with $1\times10^6$ B16 cells and subcutaneously in the left flank with $1\times10^4$, $1\times10^5$ or $1\times10^6$ B16 cells. The tumor developing in the left flank represents a distant metastasis which may not develop into a tumor lesion if the injection of $HSV_{\alpha GT}$ into the right flank lesion converts it into a vaccine that elicits a systemic protective anti-tumor response. When the right flank tumor reaches the size (diameter) of 4-5 mm (within 5-6 days) it is injected with 0.1 ml suspension $HSV_{\alpha GT}$ at an amount that is twice the amount that induces 100% cytolysis of the melanoma lesion. Oncolytic HSV lacking the inserted α1,3GT gene is used as control virus incapable of inducing the expression of alpha-gal epitopes. The growth of the tumor in the left flank is monitored for 2 months. Conversion of the tumor injected with $HSV_{\alpha GT}$ into a vaccine results in prevention of the distant metastases in the left flank from growing into a detectable lesion when the left flank is injected with $1\times10^4$, $1\times10^5$ or $1\times10^6$ B16 cells. The prevention of tumor growth is thought to be more effective (i.e. prevention of higher number of tumor cells from developing into a lesion in the left flank) when the tumor in the right flank is injected with $HSV_{\alpha GT}$ than with HSV lacking the α1,3GT gene.

Example 7: Efficacy of $HSV_{\alpha GT}$ or Infected Lesions in Eliciting a Protective Anti-Tumor Immune Response Against Challenging Tumor Cells Anti-Gal producing alpha 1,3-galactosyltransferase knockout mice are injected subcutaneously in the right abdominal flank with $1\times10^6$ B16 cells. When the tumor reaches the size (diameter) of 4-5 mm (within 5-6 days) it is injected with 0.1 ml suspension $HSV_{\alpha GT}$ at an amount that is twice the amount that induces 100% cytolysis of the melanoma lesion. Oncolytic HSV lacking the inserted α1,3GT gene is used as control virus incapable of inducing the expression of alpha-gal epitopes. Three weeks after the injection of the oncolytic virus into the right flank lesion, the left flank is injected with $0.3\times10^6$, $1\times10^6$, $3\times10$, or $10\times10^6$ B16 cells as tumor challenge. The induction of a protective anti-tumor immune response as a result of injection of $HSV_{\alpha GT}$ into the right flank tumor (which converts the tumor into a vaccine) results in prevention of the challenging tumor cells in the left flank from developing into a tumor lesion. The prevention of tumor growth is more effective (i.e. prevention of higher number of challenging tumor cells from developing into a lesion) when the tumor in the right flank is injected with $HSV_{\alpha GT}$ than with HSV lacking the α1,3GT gene.

Example 8: Production and Efficacy of a Replication Competent Oncolytic Adenovirus that Encodes a Functional Alpha 1,3-Galactosyltransferase Gene The present study describes the production of an Ad5/3-Δ24-αGT CRAd (CRAd-αGT), in which the E3 gene was replaced with the murine alpha 1,3-galactosyltransferase (α1,3GT) gene. α1,3GT synthesizes the carbohydrate antigen galactose-alpha-1,3-galactosyl-beta-1,4-N-acetyl-glucosamine-R (alpha-gal). When the virus replicates, the α1,3GT protein is produced along with the viral proteins, the αGT protein subsequently catalyzes the production of alpha-gal. Cell surface alpha-gal is complexed by anti-Gal antibodies, promoting immune activation and uptake of the immune complexes by antigen presenting cells.

Materials and Methods

Cell Lines

A549 (human lung carcinoma) and A375 (human melanoma) cell lines were purchased from the European Collection of Authenticated Cell Cultures (ECCAC). A549 cells were maintained in F-12K+10% fetal bovine serum (FBS). A375 cells were maintained in Dulbecco's Modified Eagle Medium (DMEM)+10% fetal bovine serum. Both cell lines were incubated at 37° C. and 5% $CO_2$.

Virus Production

Figure 6:
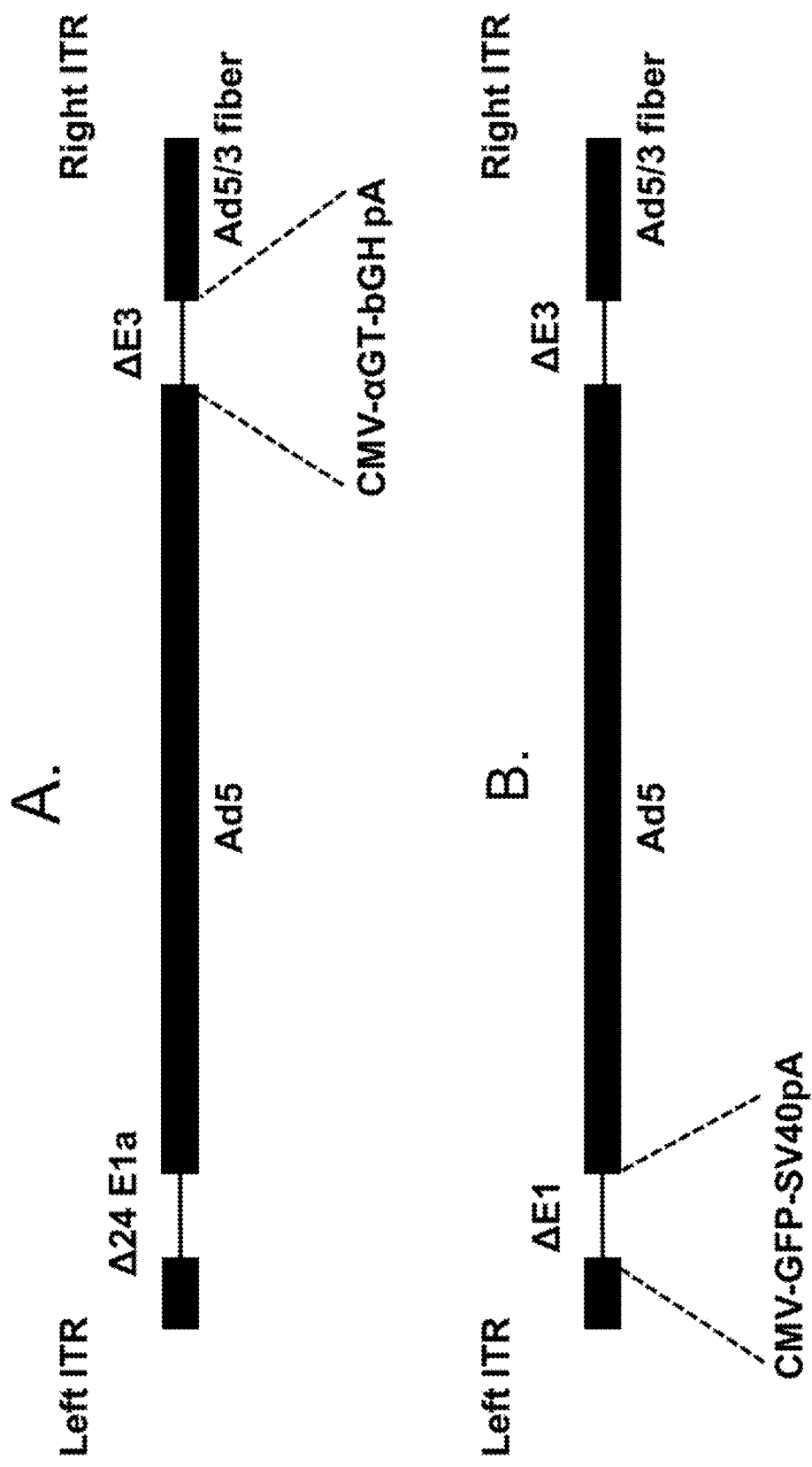
FIG. 6: Provides the genomic structures of CRAd-$\alpha$GT (A) and CRAd-GFP (B). The Ad5 genomic sequence was modified to express the fiber knob of Ad3. The E3 or E1 sequences were modified by deletion or replacement with the nucleotide sequences of the $\alpha$1,3GT or GFP genes, respectively.

Virus production was performed under contract by Imanis Life Sciences (Rochester, Minneapolis, US). Virus construction was performed using established shuttle and large adenoviral plasmids and recombinant DNA methods exactly as described in detail (Danthinne and Werth, 2000; Danthinne, 2001). In order to create the CRAd-αGT, the 1.1 Kb murine α1,3GT gene (GenBank accession number M85153) was synthesized by Integrated DNA Technologies (IDT) and cloned into an Ad5 E3 shuttle vector with a CMV promotor 5' of the α1,3GT sequence. In a cosmid encoding the Ad5 genome, with the fiber knob sequence replaced with that of Ad3, the 24-bp sequence encoding the LTCHEAGF (SEQ ID NO: 3) amino acid sequence was deleted from region E1a. The E3 sequence was deleted from the Ad5/3 cosmid and replaced with the CMV-αGT sequence, subcloned from the shuttle vector. To create a control, CRAd, the green fluorescent protein (GFP) coding sequence was synthesized by IDT and cloned into an Ad5 E1 shuttle vector with a CMV promotor 5' of the GFP sequence. The E1 sequence was deleted from the Ad5/3 cosmid and replaced with the CMV-GFP sequence, subcloned from the shuttle vector. The E3 region was deleted. The chimeric virus structures are shown in FIG. 6.

HEK 293 cells were transfected with the chimeric virus cosmids and, after 48 hours incubation, crude lysates prepared. For virus amplification, HEK 293 cells were seeded in 15 cm dishes and incubated overnight at 37° C., 5% $CO_2$. The next day, the cells were infected with the crude lysate from virus-infected cells and incubated for 48 hours at 37° C., 5% $CO_2$, after which time the cells and supernatant were harvested.

Virus particles were released from infected cells by three freeze-thaw cycles and recovered from the cell supernatant by ammonium sulphate precipitation (Schagen et al., 2000). Virus purification was performed by cesium chloride (CsCl) density gradient centrifugation. Briefly, the crude virus preparation was loaded onto a two-step CsCl gradient in a SW28 Beckman centrifuge tube and centrifuged for 2 hours at 20,000 rpm. The virus band was collected and loaded on to a continuous CsCl gradient and centrifuged again. The final virus band was collected and immediately dialyzed against 4×0.5 L GTS buffer (2.5% glycerol, 25 mM NaCl, 20 mM Tris-HCl pH 8.0) for 18 hours at 4° C. Approximately 1 ml dialysed virus suspension was collected and filtered through a 0.22 μm Supor membrane (Pall) then frozen at −70° C.

Virus concentration was determined using the OD260-SDS method and the extinction coefficient of $1.1×10^{12}$ virus particles (VP) per absorbance 260 unit in the presence of SDS. The virus concentrations were found to be $3.6×10^{12}$ VP/ml for CRAd-αGT and $2.9×10^{12}$ VP/ml for CRAd-GFP. The purity of the virus preparations was determined by A260/A280 and A320/A260 ratios and was found to be within the range associated with pure virus (1.2 to 1.4 and 0.22 to 0.27 respectively) for both viruses.

The virus titer was determined by endpoint dilution assay (TCID50) using the well-established Reed-Muench method (Reed and Muench, 1938). Briefly, HEK293 cells were seeded into 24-well plates and incubated overnight at 37° C. The next day, a 10-fold dilution series of CsCl-purified virus stock was added to the seeded HEK293 cells and the cells incubated at 37° C., 5% $CO_2$ for 14 days. Wells were scored for the presence of cytopathic effects (CPE) by visual assessment under the microscope and the TCID50 calculated using the Reed-Muench equation (Reed and Muench, 1938). The virus titer was determined to be $6.8×10^{11}$ TCID50/mL for CRAd-αGT and $2.7×10^{11}$ TCID50/ml for the CRAd-GFP.

Determination of Cell Killing by CRAd-αGT

Sub-confluent monolayers of A549 and A375 cells were harvested from tissue culture flasks using cell dissociation solution (CDS, Sigma-Aldrich). The cells were counted using a hemocytometer and live cells distinguished from dead by Trypan Blue exclusion. The cells were diluted in culture medium and added to sterile 96-well white, tissue culture plates at 90 μl/well to give either $5×10^3$ or $1×10^4$ cells/well.

Each virus was diluted 1:3 in phosphate buffered saline (PBS)+10% FBS to provide working stock solutions of $1.2×10^{12}$ VP/ml for CRAd-αGT and $9.67×10^{11}$ VP/ml for CRAd-GFP. The working stocks were serially diluted 1 in 5 in PBS+10% FBS to generate a titration series of $1.2×10^{12}$-$1.2×10^5$ VP/ml for CRAd-αGT and $9.67×10^{11}$-$9.9×10^4$ for CRAd-GFP. The titration series were diluted 1:10 into the assay plates (10 μl per well of virus to the 90 μl seeded cells) and the plates incubated for 72 hours at 37° C./5% $CO_2$. Cell viability was determined using Cell Titre Glo luminescent cell viability reagent (Promega), according to manufacturer's instructions, and the plates read on an EnVision 2102 plate reader (Perkin Elmer). Raw luminescence units (RLU) were plotted against log virus particles/ml.

To visualize the cytolytic effect of the CRAd-αGT virus, A549 and A375 cells seeded into clear 96-well or 24-well plates, as detailed above and below, and infected with various dilutions of CRAd-αGT and CRAd-GFP, again detailed above and below, were assessed under a light microscope. Images of cells were taken with a YenCam 10 (Yenway) and supporting software.

Determination of Anti-Gal Binding to Ad/3-Δ24-αGT CRAd Infected Human Cancer Cells A549 and A375 cells were harvested from tissue culture flasks as described above. After counting, the cells were diluted in culture medium and added to 24-well, tissue culture plates in a volume of 540 µl/well, which equated to $3 \times 10^4$ cells/well.

Each virus was diluted 1:10,000 in PBS+10% FBS (1:100 and then 1:100) to provide solutions of $3.6 \times 10^8$ VP/ml for CRAd-αGT and $2.9 \times 10^8$ for CRAd-GFP. These solutions were diluted 1:25 twice in PBS+10% FBS to give virus concentrations of $1.44 \times 10^7$ and $5.8 \times 10^5$ VP/ml for CRAd-αGT and $1.16 \times 10^7$ and $4.6 \times 10^5$ VP/ml for CRAd-GFP. The three virus dilutions were diluted a further 1:10 onto the seeded cells (60 µl virus to the 540 µl cells per well). An equal volume of PBS+10% FBS alone was added to wells serving as no virus controls.

The plates were incubated for 72 hours. At the end of the incubation the presence of alpha-gal antigen on the surface of infected cells was determined by flow cytometry. Infected and uninfected (no virus control) cells were harvested from 24-well plates using CDS, washed in PBS+0.5% BSA and incubated with 40 µg/ml monoclonal M86 human IgG1 anti-Gal antibody (Absolute Antibody), diluted in PBS+0.5% BSA, at 4° C. for 1 hour. The cells were washed again in PBS+0.5% BSA and then incubated with allophycocyanin (APC)-conjugated anti-human IgG (Biolegend), diluted in PBS+0.5% BSA at 4° C. for 30 minutes in the dark. Cells were washed with PBS+0.5% BSA and analyzed on a Beckman Coulter FC500 flow cytometer. Unstained cells were used to set the voltages for forward scatter, side scatter and fluorescent channels 1 and 4. GFP (channel 1) and APC (channel 4) signals were recorded for test samples. Single color controls were used to set the compensation.

Results

CRAd-αGT Lyses Human Cancer Cells

Figure 7:
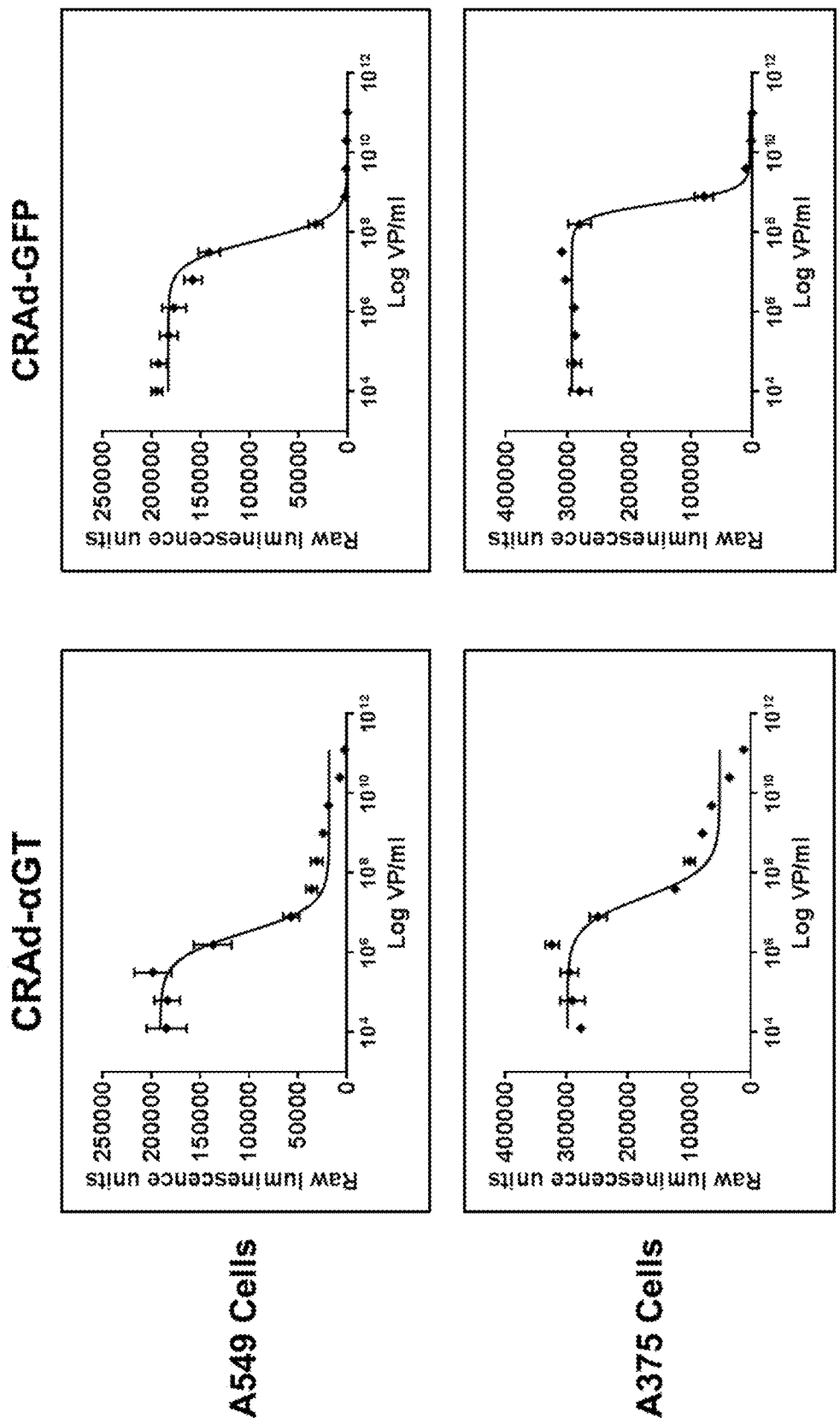
FIG. 7: Quantification of human cancer cell viability after infection with CRAd-$\alpha$GT. A549 and A375 cells were seeded in 96-well plates, infected with a serial titration of virus starting from 1.2×10$^{11}$ virus particles (VP)/ml CRAd-$\alpha$GT or 9.7×10$^{10}$ VP/ml CRAd-GFP control virus and incubated for 72 hours. Cell viability was quantified using a luminescent cell viability assay Cell Titre Glo (Promega).

The cytolytic effects of CRAd-αGT and control CRAd-GFP on A549 and A375 cells were quantified using a plate-based cell viability assay (FIG. 7). The reduction in cell viability observed in wells where cells were infected with either CRAd-αGT or CRAd-GFP was dependent on the concentration of virus. The number of CRAd-αGT virus particles required to reduce cell viability by 50% was lower than for the control CRAd-GFP virus. This is in line with the virus titer measured by TCID50 assay (see Materials and Methods section above).

Figure 8:
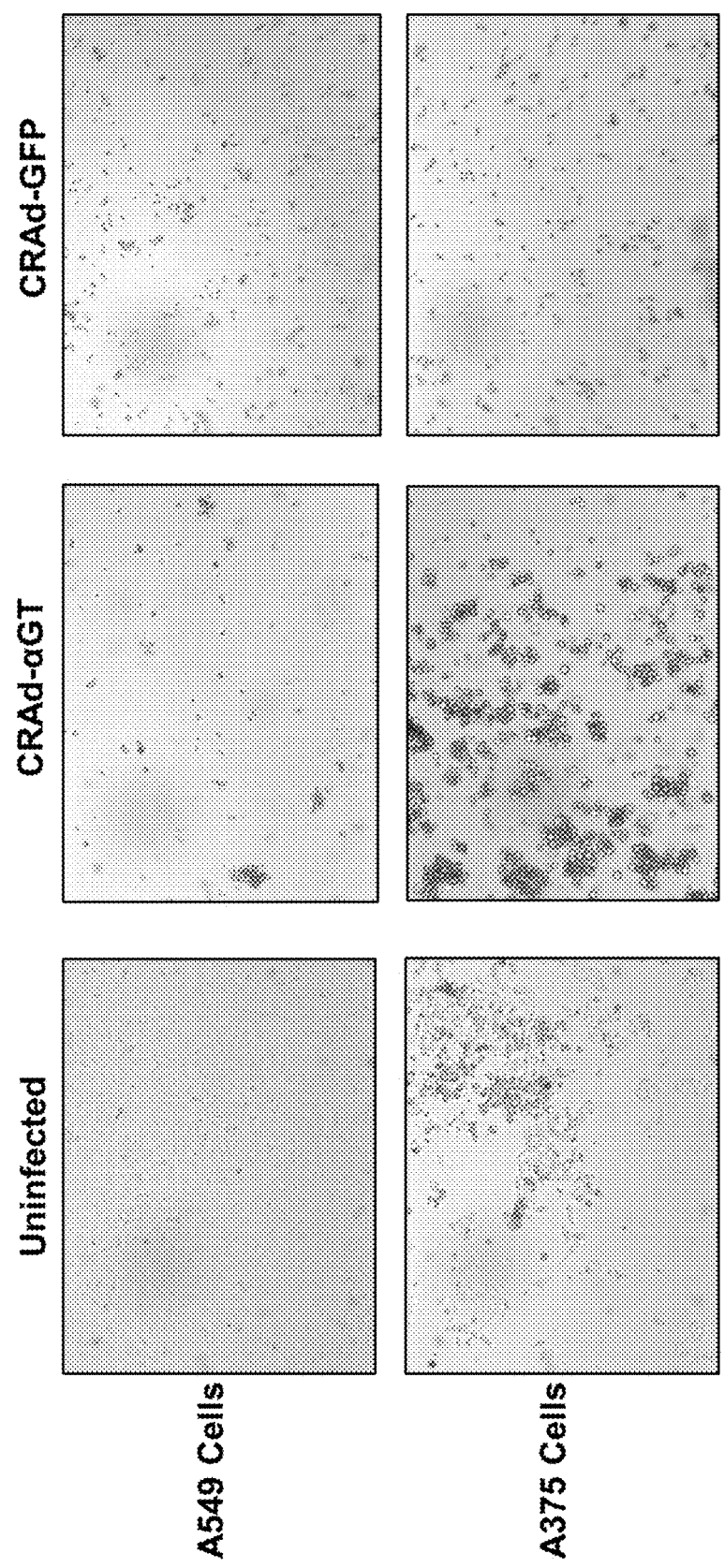
FIG. 8: Visualization of human cancer cell viability after infection with CRAd-$\alpha$GT. A549 (lung carcinoma) and A375 (melanoma) cells were seeded in 24-well plates, infected with 3.6×10$^7$ virus particles (VP)/ml CRAd-$\alpha$GT or 1.9×10$^{10}$ VP/ml CRAd-GFP control virus and incubated for 72 hours. Visualization was performed using light microscopy at 10× magnification.

The cytolytic effect of CRAd-αGT in A549 and A375 human cancer cells was visualized by light microscopy and compared to CRAd-GFP (FIG. 8). Cells that were infected with either CRAd-αGT or CRAd-GFP, and then incubated for 72 hours, were killed by both viruses. Uninfected cells were healthy, with no evidence of lysis.

CRAd-αGT Infected Cells Bind Anti-Gal Antibodies

Figure 9:
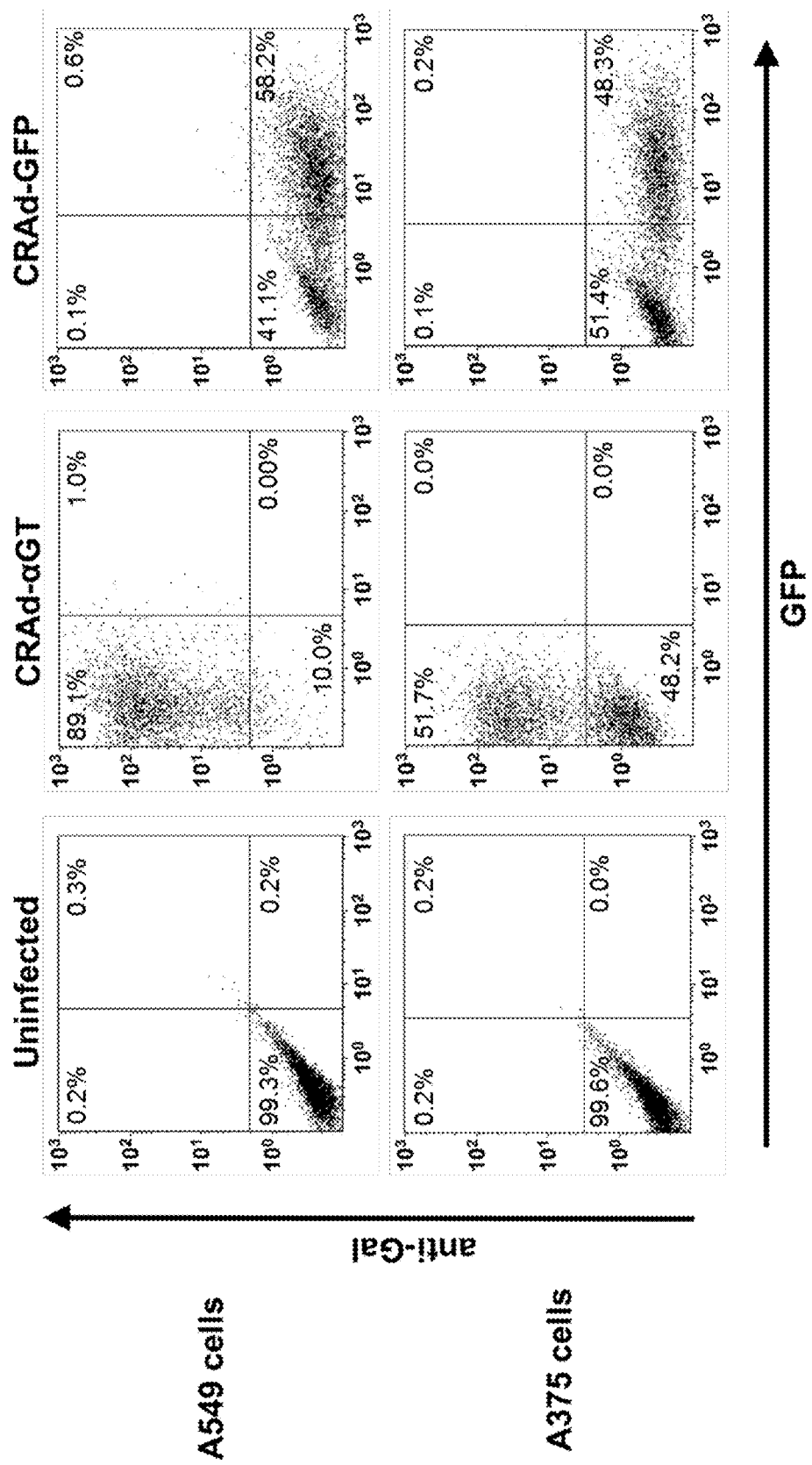
FIG. 9: Analysis of anti-Gal binding to human cancer cells after infection with CRAd-$\alpha$GT. A549 and A375 cells were infected with either 1.44×10$^6$ virus particles (VP)/ml CRAd-$\alpha$GT or 1.16×10$^6$ VP/ml CRAd-GFP control virus. The cells were analyzed for anti-Gal binding and GFP expression by flow cytometry.

To investigate whether infection of cells with CRAd-αGT results in expression of a catalytically active α1,3GT protein and subsequent expression of alpha-gal at the cell surface, binding of alpha-gal-specific anti-Gal antibodies to the CRAd-αGT infected cells was determined and compared to the binding of anti-Gal antibodies to CRAd-GFP and uninfected cells using flow cytometry (FIG. 9). Cells that were infected with CRAd-αGT were strongly bound by anti-Gal, but were negative for GFP expression. Conversely, cells that were infected with CRAd-GFP were negative for anti-Gal binding, but were positive for GFP expression. Uninfected cells were negative for both anti-Gal binding and GFP expression.

CONCLUSIONS

Infection of human non-small cell lung carcinoma (A549) and melanoma (A375) cells with CRAd-αGT resulted in cell lysis and death. The cell lysis occurs as a consequence of CRAd-αGT replication, which is selective for cancer cells due to the deletion of the 24-bp region from the viral E1a gene (Fueyo et al., 2000).

In addition to cell lysis, infection of cancer cells with the CRAd-αGT resulted in the specific binding of anti-Gal antibodies to the cell surface, whereas anti-Gal did not bind to uninfected or CRAd-GFP infected cells. As anti-Gal specifically binds to the alpha-gal epitope, we can conclude that replication of the CRAd-αGT in cancer cells results in expression of catalytically active α1,3GT enzyme, which subsequently catalyzes the synthesis of alpha-gal.

The binding of anti-Gal antibodies to alpha-gal expressing dying tumor cells and tumor cell debris, created by the oncolytic effect of the virus, will enhance the adaptive immune response to the tumor neoantigens. Antigen presenting cells (APCs) bearing activating Fcγ receptors engulf tumor cell debris and dead cells complexed with anti-Gal IgG via activating Fcγ receptors. Activation of Fcγ receptors on APCs leads to APC activation, maturation and enhanced presentation of antigen to T cells (Regnault et al., 1999; Rafiq et al., 2002; Platzer et al., 2014).

REFERENCES

Bramante et al. (2015). Int. J. Cancer 137: 1775-1783.
Danthinne (2001). Biotechniques 30: 612-6, 618-9.
Danthinne and Werth (2000). Gene Ther. 7: 80-7.
Fueyo et al. (2000). Oncogene 19: 2-12.
Kanerva et al. (2013). Clin. Cancer Res. 19: 2734-2744.
Kanerva et al. (2003). Mol. Ther. 8: 449-458.
Kanno et al. (2012). Anticancer Res. 32: 4891-5.
Kim et al. (2013). Gynecol. Oncol. 130: 518-24.
Koski et al. (2010). Mol. Ther. 18: 1874-84.
Platzer (2014). Front. Immunol. 5: 140.
Rafiq et al. (2002). J. Clin. Invest. 110: 71-9.
Reed and Muench (1938). Am. J. Epidemiol. 27: 493-497.
Regnault et al. (1999). J. Exp. Med. 189: 371-80.
Schagen et al. (2000). Gene Ther. 7: 1570-4.
Sherr (1996). Science 274: 1672-7.
Ulasov et al. (2006). Hum. Gene Ther. 17: 556-64.

The invention claimed is:

1. A method of inducing an immune response in an individual suffering from a tumor which comprises the steps of
   i) expressing an endogenous enzyme delivered by an oncolytic virus comprising a nucleic acid encoding an alpha 1,3-galactosyltransferase enzyme in at least one cancer cell of the individual to modify cell membrane glycosylation; and
   ii) inducing lysis of the at least one cancer cell resulting from administration of the oncolytic virus, wherein the administration is by direct injection into the tumor.

2. The method according to claim 1, wherein the oncolytic virus is administered in an effective amount to infect at least one cancer cell in the individual.

3. The method according to claim 1, which is directed to treating an individual with cancer or an individual with a tumor.

4. The method according to claim 1, wherein the oncolytic virus comprises a recombinant binding domain specific for a tumor stem cell marker.

5. The method according to claim 1, wherein the oncolytic virus is replication restricted.

6. The method according to claim 1, wherein the oncolytic virus is an RNA or DNA based virus of human or non-human origin.

7. The method according to claim 6, wherein the oncolytic virus is an adenovirus.

8. The method according to claim 7, wherein the oncolytic virus is a conditionally replicating adenovirus (CRAd).

9. The method according to claim 8, wherein the conditionally replicating adenovirus is an Ad5/3 chimeric virus.

10. The method according to claim 9, wherein the Ad5/3 chimeric virus additionally comprises a 24-base pair deletion (Δ24) in constant region 2 (CR2) of the viral immediately early (E1a) gene (Ad5/3-Δ24 CRAd).

11. The method according to claim 1, wherein the oncolytic virus is an Ad5/3-Δ24-αGT CRAd (CRAd-αGT).

12. A method of inducing a protective anti-tumor immune response in an individual suffering from a tumor comprising administering to the individual a therapeutically effective amount of an oncolytic virus comprising a nucleic acid encoding an alpha 1,3-galactosyltransferase enzyme, wherein the administering is by direct injection into the tumor.

* * * * *